(12) United States Patent
Ito

(10) Patent No.: US 11,280,994 B2
(45) Date of Patent: Mar. 22, 2022

(54) OPTICAL UNIT AND ENDOSCOPE

(71) Applicant: OLYMPUS CORPORATION, Tokyo (JP)

(72) Inventor: Tadashi Ito, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 952 days.

(21) Appl. No.: 16/008,194

(22) Filed: Jun. 14, 2018

(65) Prior Publication Data

US 2018/0292641 A1 Oct. 11, 2018

Related U.S. Application Data

(63) Continuation of application No. PCT/JP2015/085596, filed on Dec. 18, 2015.

(51) Int. Cl.
*A61B 1/00* (2006.01)
*G02B 23/24* (2006.01)
*A61B 1/05* (2006.01)
*G02B 7/04* (2021.01)

(52) U.S. Cl.
CPC ...... *G02B 23/2484* (2013.01); *A61B 1/00096* (2013.01); *A61B 1/00117* (2013.01);
(Continued)

(58) Field of Classification Search
CPC .. G02B 23/2484; G02B 23/2407; G02B 7/04; A61B 1/00117; A61B 1/00174; A61B 1/00188; A61B 1/0064
See application file for complete search history.

(56) References Cited

U.S. PATENT DOCUMENTS 5,654,848 A * 8/1997 Maiers ................. G11B 21/083
360/98.01
5,836,867 A * 11/1998 Speier ................ A61B 1/00126
600/112
(Continued)

FOREIGN PATENT DOCUMENTS

JP S61039235 A 2/1986
JP H10010401 A 1/1998
(Continued)

OTHER PUBLICATIONS

International Search Report dated Mar. 22, 2016 issued in PCT/JP2015/085596.
(Continued)

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

An optical unit includes: a fixing portion including a front frame portion that holds an object-side fixed lens group, a rear frame portion that holds an image-side fixed lens group or an image sensor, and a fixing portion main body formed by using a non-magnetic material; a moving portion that holds a moving lens group and that is arranged on an inner side of the fixing portion main body so as to be slidable with respect to the fixing portion main body; and a voice coil motor configured to move the moving portion along a direction of the optical axis relative to the fixing portion main body, and including a magnetic portion magnetized in a direction intersecting an optical axis of the object-side fixed lens group, and a coil located on an outer side of the fixing portion main body with respect to the magnetic portion.

15 Claims, 16 Drawing Sheets

(52) U.S. Cl.
CPC ...... *A61B 1/00174* (2013.01); *A61B 1/00188* (2013.01); *A61B 1/051* (2013.01); *G02B 7/04* (2013.01); *G02B 23/2407* (2013.01); *G02B 23/2476* (2013.01); *A61B 1/00064* (2013.01)

(56) References Cited

U.S. PATENT DOCUMENTS

| | | | |
|---|---|---|---|
| 2012/0314308 A1* | 12/2012 | Ikushima | G02B 27/646 |
| | | | 359/814 |
| 2016/0341950 A1* | 11/2016 | Kono | G02B 7/08 |
| 2017/0030405 A1 | 2/2017 | Konishi | |
| 2017/0047811 A1 | 2/2017 | Konishi | |
| 2018/0172946 A1* | 6/2018 | Fuse | G03B 13/36 |

FOREIGN PATENT DOCUMENTS

| | | | |
|---|---|---|---|
| JP | H10150759 A | 6/1998 | |
| JP | H10179505 A | 7/1998 | |
| JP | 2010-044166 A | 2/2010 | |
| JP | 2010072149 A | 4/2010 | |
| JP | 2012529066 A | 11/2012 | |
| JP | 2013127492 A | 6/2013 | |
| JP | 2014048320 A | 3/2014 | |
| JP | 2015055116 A | 3/2015 | |
| JP | 2015148704 A | 8/2015 | |
| WO | 2010058639 A1 | 5/2010 | |
| WO | WO-2010058639 A1 * | 5/2010 | ............... G02B 7/08 |
| WO | 2011075892 A1 | 6/2011 | |
| WO | 2015118711 A1 | 8/2015 | |
| WO | WO-2015118711 A1 * | 8/2015 | |
| WO | 2015163377 A1 | 10/2015 | |

OTHER PUBLICATIONS

Japanese Office Action dated Sep. 3, 2019 in Japanese Patent Application No. 2017-556312.

* cited by examiner

OPTICAL UNIT AND ENDOSCOPE

CROSS-REFERENCE TO RELATED APPLICATION

This application is a continuation of International Application No. PCT/JP2015/085596, filed on Dec. 18, 2015, the entire contents of which are incorporated herein by reference.

BACKGROUND

The present disclosure relates an optical unit and an endoscope.

In the related art, there is a disclosed technique that uses an electromagnetic driven actuator, i.e., a voice coil motor, that includes a moving lens unit in which a moving lens group is provided and that uses a coil and magnets as a zoom function for changing a shooting magnification or a focusing function for focusing by moving the moving lens unit forward and backward (for example, see Japanese Laid-open Patent Publication No. 2015-148704). Japanese Laid-open Patent Publication No. 2015-148704 discloses a moving magnet (MM) type optical unit that includes a moving portion in which a moving lens group is provided; a fixing portion that holds lenses and that fixes the moving portion so as to move forward and backward; a front frame portion that is provided on the side of an object of shooting in the optical axis direction and that holds the lenses; and a rear frame portion that is provided on the side opposite to the object of shooting in the optical axis direction and that holds the lenses. Furthermore, a magnet is provided in the moving portion and a coil is provided in the fixing portion.

SUMMARY

An optical unit according to one aspect of the present disclosure includes: a fixing portion including a front frame portion that holds an object-side fixed lens group, a rear frame portion that holds an image-side fixed lens group or an image sensor, and a fixing portion main body that is formed by using a non-magnetic material and that holds the front frame portion and the rear frame portion; a moving portion that holds a moving lens group between the object-side fixed lens group and the image-side fixed lens group or the image sensor and that is arranged on an inner side of the fixing portion main body in a radial direction so as to be slidable with respect to the fixing portion main body; and a voice coil motor configured to move the moving portion along a direction of the optical axis relative to the fixing portion main body, the voice coil motor including a magnetic portion that is arranged in the moving portion and that has been magnetized in a direction intersecting an optical axis of the object-side fixed lens group, and a coil that is arranged in the fixing portion main body and that is located on an outer side of the fixing portion main body in the radial direction with respect to the magnetic portion.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the following, embodiments of the present disclosure will be described.

First Embodiment

Figure 1:
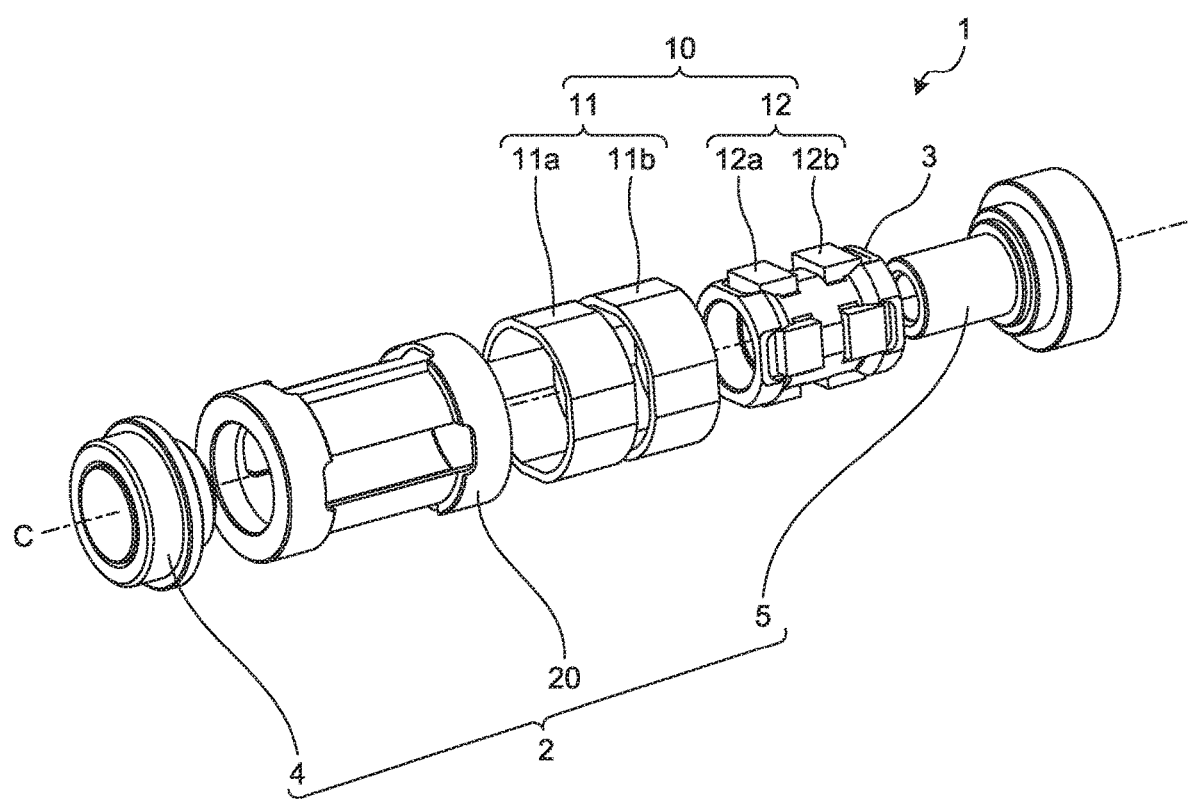
FIG. 1 is an exploded perspective view illustrating the configuration of an optical unit according to a first embodiment.
Figure 2:
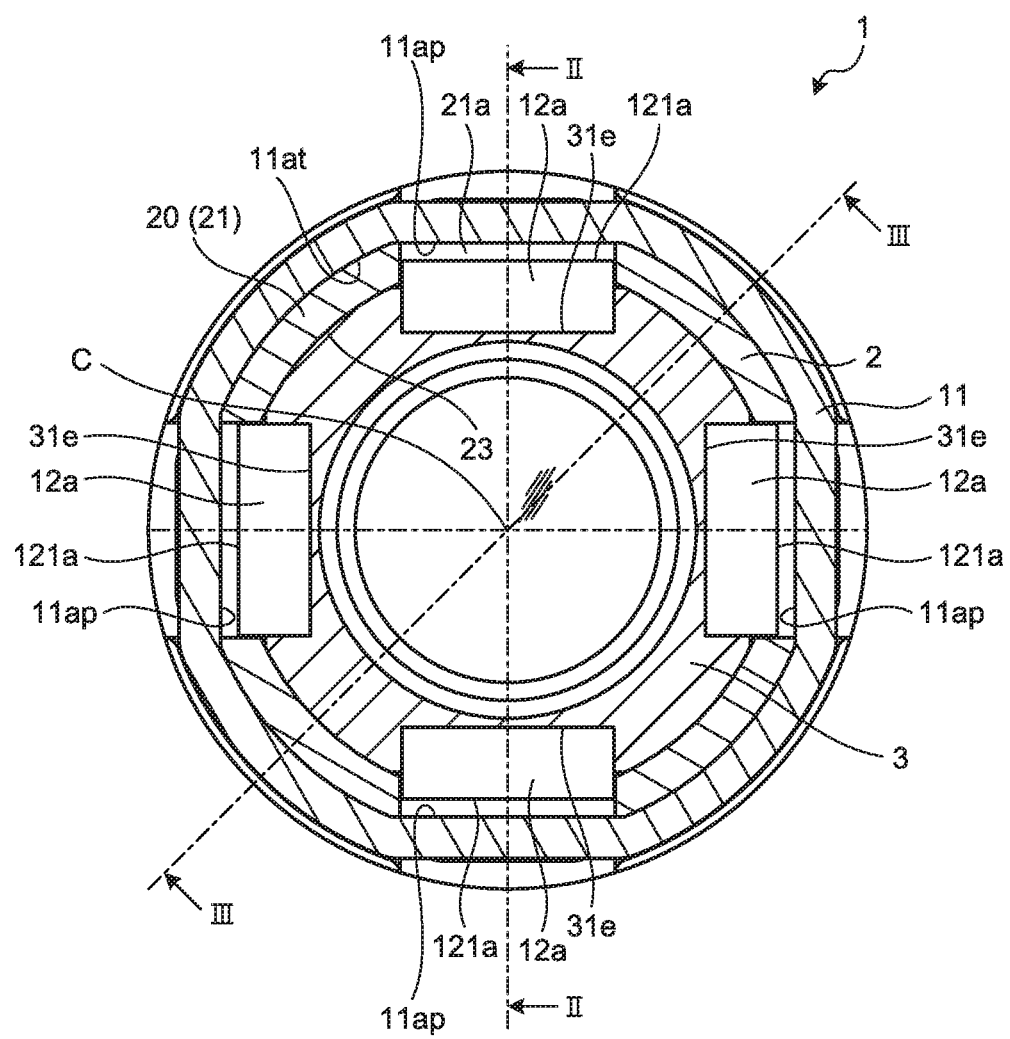
FIG. 2 is a sectional view illustrating the configuration of a relevant part of the optical unit according to the first embodiment.
Figure 3:
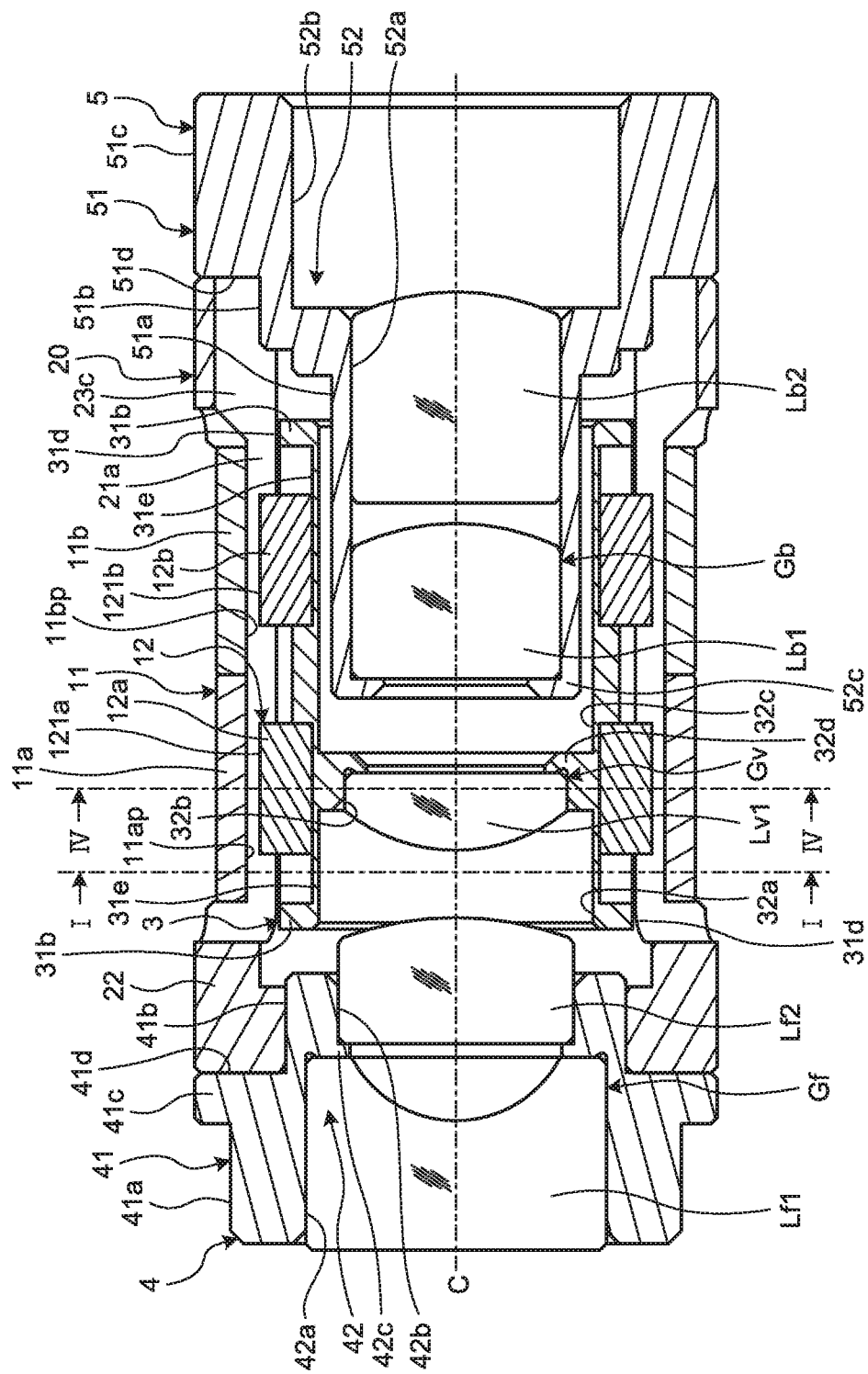
FIG. 3 is a sectional view of the optical unit viewed at a sectional plane taken along line II-II in FIG. 2.
Figure 4:
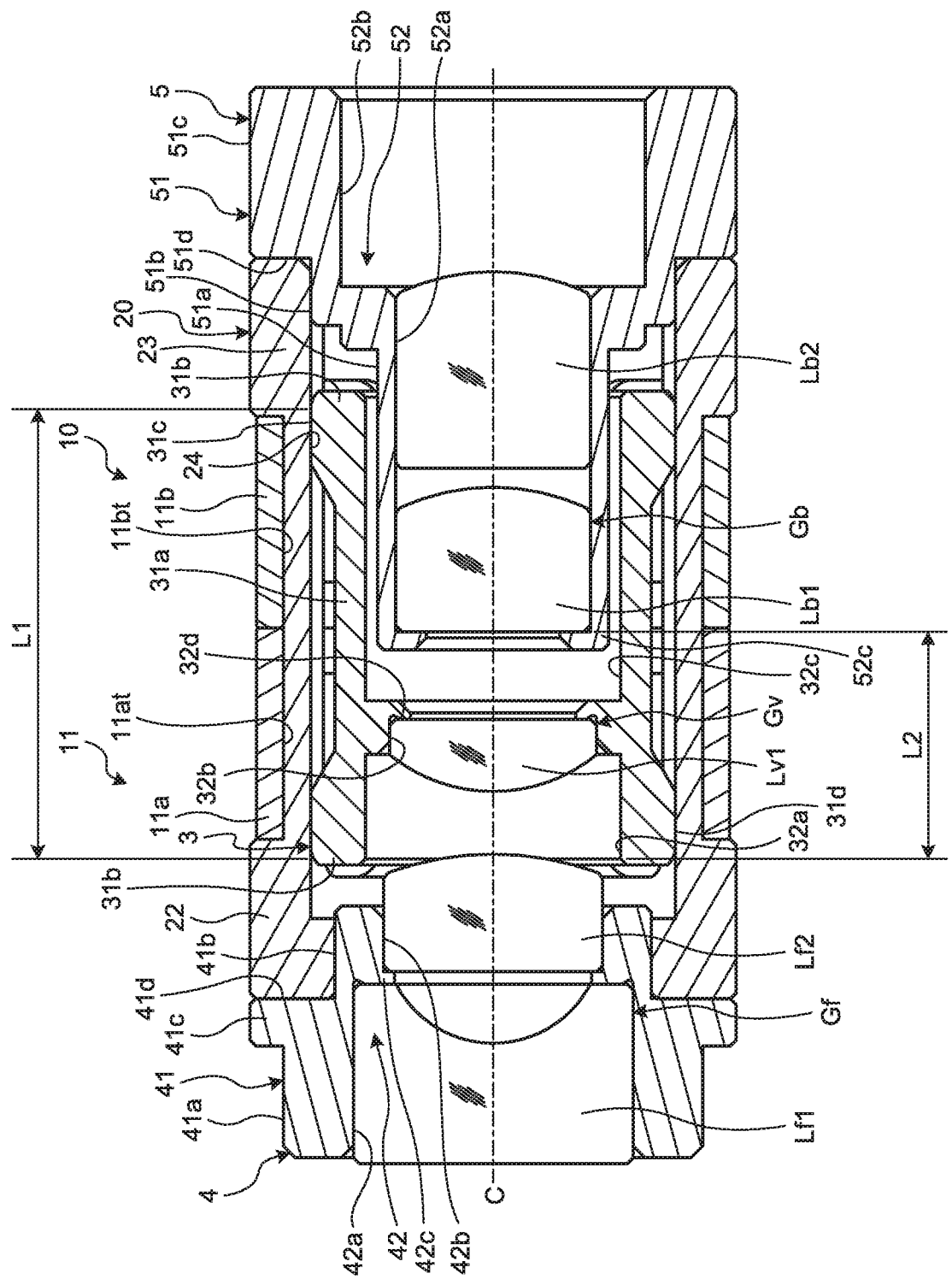
FIG. 4 is a sectional view of the optical unit viewed at a sectional plane taken along line III-III in FIG. 2.

FIG. 1 is an exploded perspective view illustrating the configuration of an optical unit according to a first embodiment. FIG. 2 is a sectional view illustrating the configuration of a relevant part of the optical unit according to the first embodiment. FIG. 3 is a sectional view of the optical unit viewed at a sectional plane taken along line II-II in FIG. 2. FIG. 4 is a sectional view of the optical unit viewed at a sectional plane taken along line III-III in FIG. 2. Furthermore, FIG. 2 is also a sectional view of the optical unit viewed at a sectional plane taken along line I-I in FIG. 3.

An optical unit 1 illustrated in FIG. 1 to FIG. 4 includes a fixing portion 2, a moving portion 3 capable of moving with respect to the fixing portion 2, a voice coil motor 10 that generates a driving force for moving the moving portion 3 with respect to the fixing portion 2.

The fixing portion 2 includes a fixing portion main body 20; a front frame portion 4 that holds an object-side fixed lens group Gf on the side closer to the object side than a moving lens group Gv held by the moving portion 3 and that is attached to the object side of the fixing portion main body 20; and a rear frame portion 5 that holds an image-side fixed lens group Gb on the side closer to the image side than the moving lens group Gv and that is attached to the image side of the fixing portion main body 20. The fixing portion main body 20, the front frame portion 4, and the rear frame portion 5 are formed by using a non-magnetic material or a material, although the material is a non-magnetic material, with relative permeability equal to or greater than 1.0.

Figure 5:
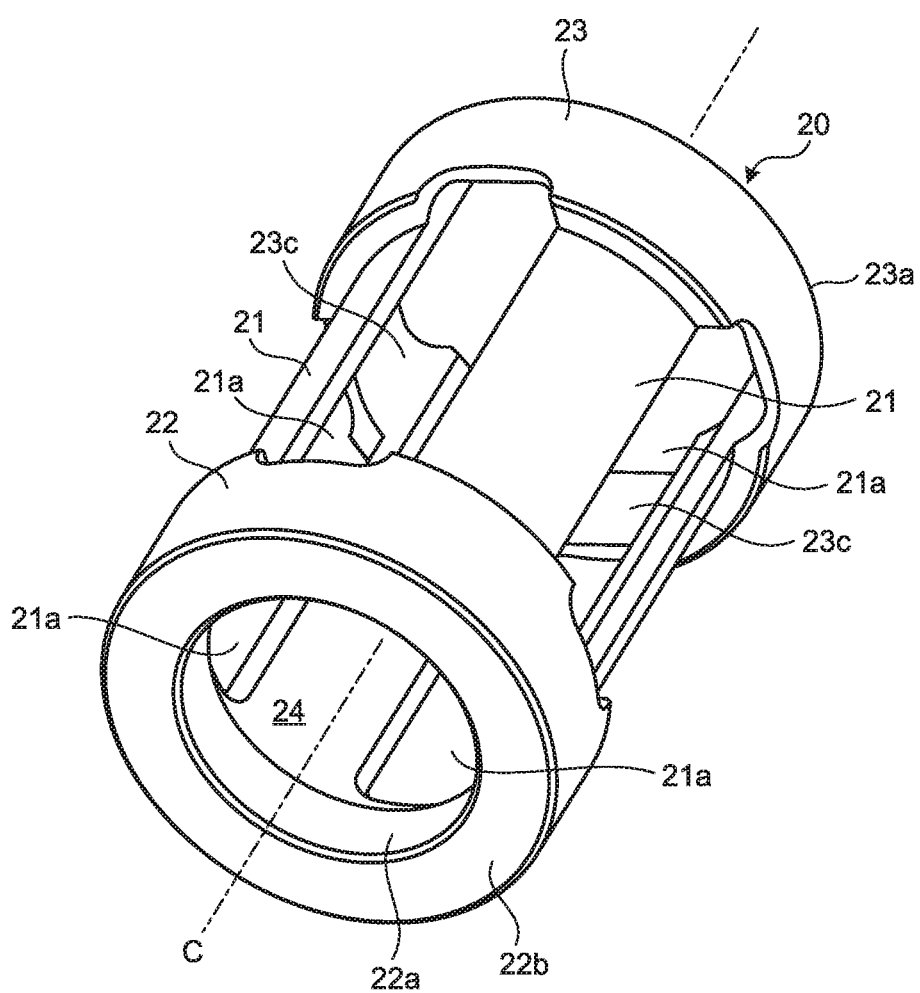
FIG. 5 is a perspective view illustrating the configuration of a fixing portion main body in the optical unit according to the first embodiment.

FIG. 5 is a perspective view illustrating the configuration of the fixing portion main body 20. The fixing portion main body 20 illustrated in FIG. 5 is formed by a cylindrical shaped member with a predetermined axis C as the center. The fixing portion main body 20 includes a tube portion 21 with the axis C as the central axis; an object-side thick portion 22 formed on the object side in the direction of the axis C with respect to the tube portion 21; and an image-side thick portion 23 formed on the opposite side of the object-side thick portion 22 in the direction of the axis C with respect to the tube portion 21. The fixing portion main body 20 is 90-degree rotationally symmetric with respect to the axis C. Hereinafter, the opposite side of the object side along the direction of the axis C is referred to as an image side.

In the tube portion 21, lightening portions 21a are formed. Specifically, the four lightening portions 21a that pass through in the radial direction of the tube portion 21 and that are disposed around the central axis C extending in the longitudinal direction of the tube portion 21 at spaces of 90 degrees in the circumferential direction. The inner surface of the tube portion 21 other than the lightening portions 21a in the radial direction is a cylindrical surface and forms a fixing-side sliding surface 24 that guides and supports the moving portion 3. The fixing-side sliding surface 24 has a shape of being divided in the circumferential direction by the lightening portions 21a.

The object-side thick portion 22 is formed so as to protrude to the outer side and the inner side of the tube portion 21 in the radial direction. The image-side thick portion 23 is formed so as to protrude to the outer side of the tube portion 21 in the radial direction. A groove 23c is formed on the fixing-side sliding surface 24 so as to protrude inward and outward than the image-side thick portion 23 in the radial direction. When the moving portion 3 is assembled, a magnet 12, which will be described later, passes through the groove 23c. Consequently, it is possible to smoothly construct the moving portion 3 with respect to the fixing portion main body 20. Furthermore, the object-side thick portion 22 and the image-side thick portion 23 may also be formed so as to be separated from the tube portion 21 and may also be attached to the tube portion 21 at the time of construction.

Figure 6:
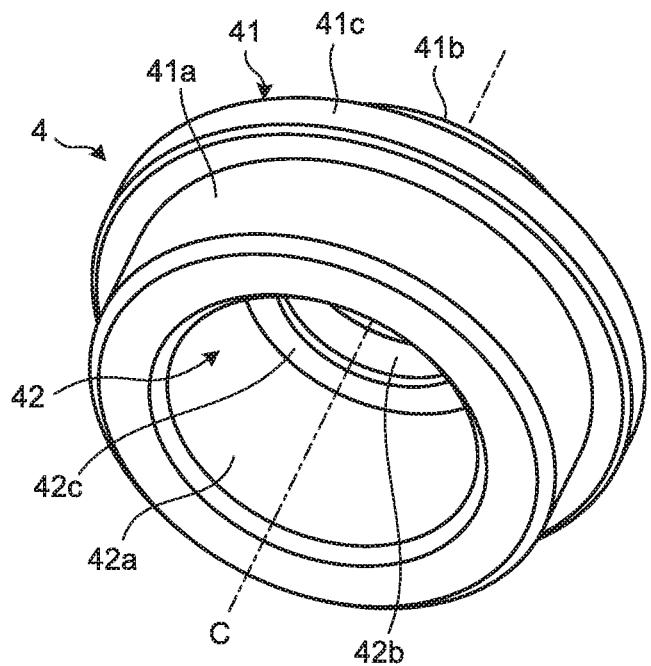
FIG. 6 is a perspective view illustrating the configuration of a front frame portion in the optical unit according to the first embodiment.
Figure 7:
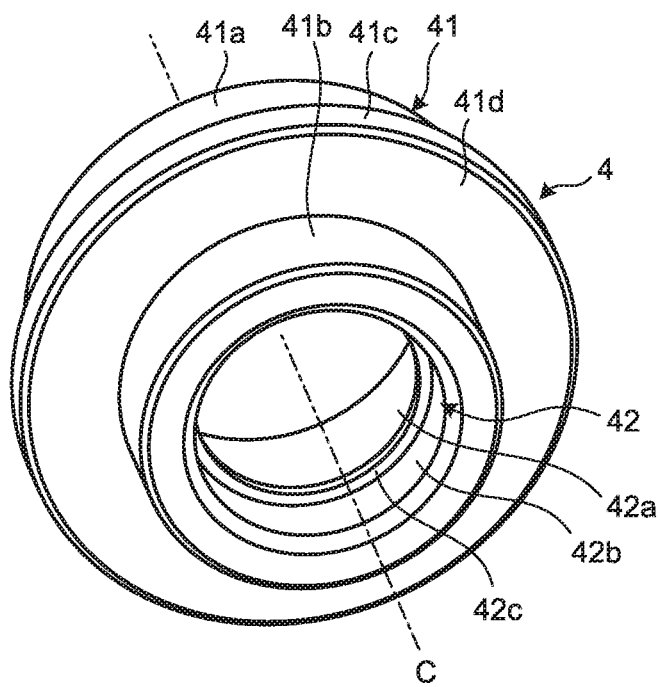
FIG. 7 is a perspective view illustrating the configuration of the front frame portion in the optical unit according to the first embodiment, viewed from the side opposite to the side illustrated in FIG. 6.

FIGS. 6 and 7 are perspective views each illustrating the configuration of the front frame portion 4 when each of which is viewed from a different side of the axis C. Furthermore, the reason for referring the central axis of the front frame portion 4 as the axis C is that the axis C matches the central axis of the fixing portion main body 20 at the time of assembly. The front frame portion 4 is a cylindrical member having an outer circumferential portion 41 and an inner circumferential portion 42. The outer circumferential portion 41 includes a first outer circumferential portion 41a, a second outer circumferential portion 41b, and an outer-circumferential-side protruding portion 41c. The inner circumferential portion 42 includes a first inner circumferential portion 42a, a second inner circumferential portion 42b, and an inner-circumferential-side protruding portion 42c.

In the outer circumferential portion 41, the diameter of the first outer circumferential portion 41a is larger than that of the second outer circumferential portion 41b. The outer-circumferential-side protruding portion 41c that protrudes outward in the radial direction and that has the largest diameter is provided between the first outer circumferential portion 41a and the second outer circumferential portion 41b.

In the inner circumferential portion 42, the diameter of the first inner circumferential portion 42a is larger than that of the second inner circumferential portion 42b. The inner-circumferential-side protruding portion 42c that protrudes inward in the radial direction and that has the smallest diameter is provided between the first inner circumferential portion 42a and the second inner circumferential portion 42b.

The front frame portion 4 holds an object-side fixed lens group Gf. The object-side fixed lens group Gf includes a front first lens Lf1 and a front second lens Lf2 that are disposed in this order from the object side. The first inner circumferential portion 42a holds the front first lens Lf1 and the second inner circumferential portion 42b holds the front second lens Lf2. It is preferable that the image side of the front first lens Lf1 and the object side of the front second lens Lf2 abut, as illustrated in FIGS. 3 and 4, against the inner-circumferential-side protruding portion 42c.

When the front frame portion 4 is inserted into the fixing portion main body 20, the front frame portion 4 is inserted, while the second outer circumferential portion 41b is brought into contact with an inner circumferential surface 22a of the object-side thick portion 22 of the fixing portion main body 20, until an end surface 22b of the object side of the fixing portion main body 20 is brought into contact with a step portion 41d between the second outer circumferential portion 41b and the outer-circumferential-side protruding portion 41c.

Figure 8:
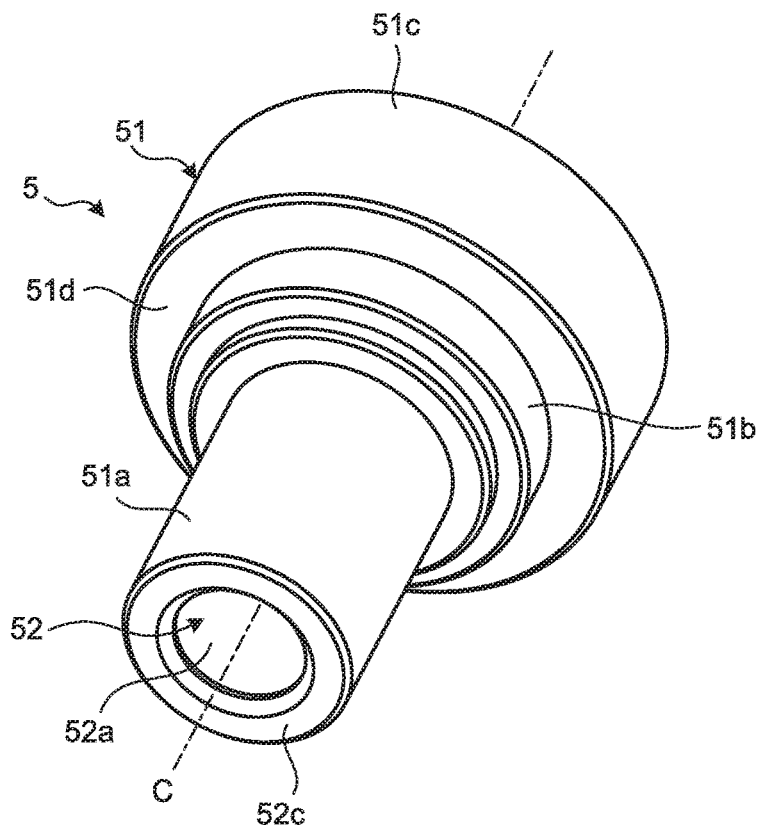
FIG. 8 is a perspective view illustrating the configuration of a rear frame portion in the optical unit according to the first embodiment.
Figure 9:
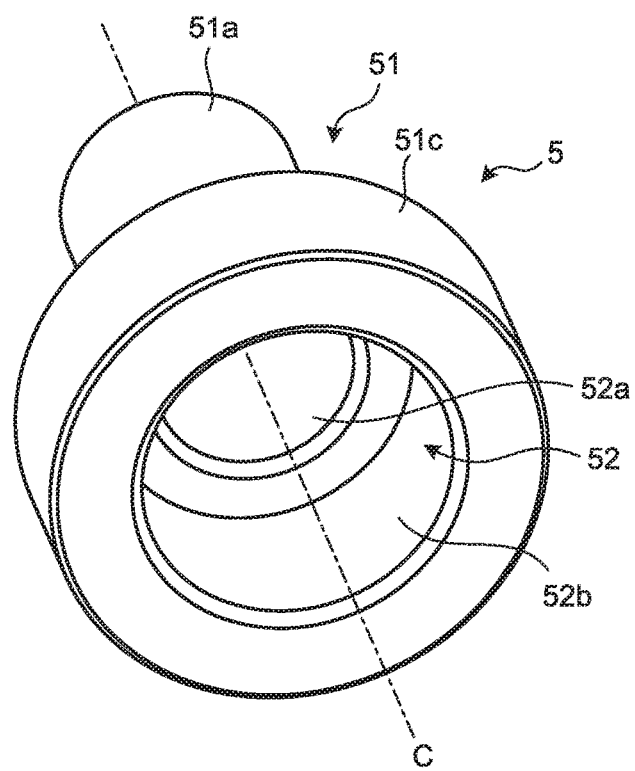
FIG. 9 is a perspective view illustrating the configuration of the rear frame portion in the optical unit according to the first embodiment, viewed from the side opposite to the side illustrated in FIG. 8.

FIGS. 8 and 9 are perspective views each illustrating the configuration of the rear frame portion 5 when each of which is viewed from each of the different sides of the axis C. Furthermore, the reason for referring the central axis of the rear frame portion 5 as the axis C is that, similarly to the front frame portion 4, the axis C matches the central axis of the fixing portion main body 20 at the time of assembly. The rear frame portion 5 is a cylindrical member having an outer circumferential portion 51 and an inner circumferential portion 52. The outer circumferential portion 51 includes a first outer circumferential portion 51a, a second outer circumferential portion 51b, and a third outer circumferential portion 51c. The inner circumferential portion 52 includes a first inner circumferential portion 52a, a second inner circumferential portion 52b, and an inner-circumferential-side protruding portion 52c.

In the outer circumferential portion 51, the diameter of the first outer circumferential portion 51a is smaller than that of the second outer circumferential portion 51b and the diameter of the second outer circumferential portion 51b is smaller than that of the third outer circumferential portion 51c.

In the inner circumferential portion 52, the diameter of the first inner circumferential portion 52a is smaller than that of the second inner circumferential portion 52b. The inner-circumferential-side protruding portion 52c that protrudes inward in the radial direction is provided in the end portion of the object side of the first inner circumferential portion 52a.

The rear frame portion 5 holds an image-side fixed lens group Gb. The image-side fixed lens group Gb includes a rear first lens Lb1 and a rear second lens Lb2. The first inner circumferential portion 52a holds the rear first lens Lb1 and the rear second lens Lb2 in this order from the object side. It is preferable that the object side of the rear first lens Lb1 abut, as illustrated in FIGS. 3 and 4, against the inner-circumferential-side protruding portion 52c.

When the rear frame portion 5 is inserted into the fixing portion main body 20, the rear frame portion 5 is inserted, while the second outer circumferential portion 51b is brought into contact with the fixing-side sliding surface 24 of the image-side thick portion 23 of the fixing portion main body 20, until an end surface 23a of the image side of the fixing portion main body 20 is brought into contact with a step portion 51d between the second outer circumferential portion 51b and the third outer circumferential portion 51c.

Figure 10:
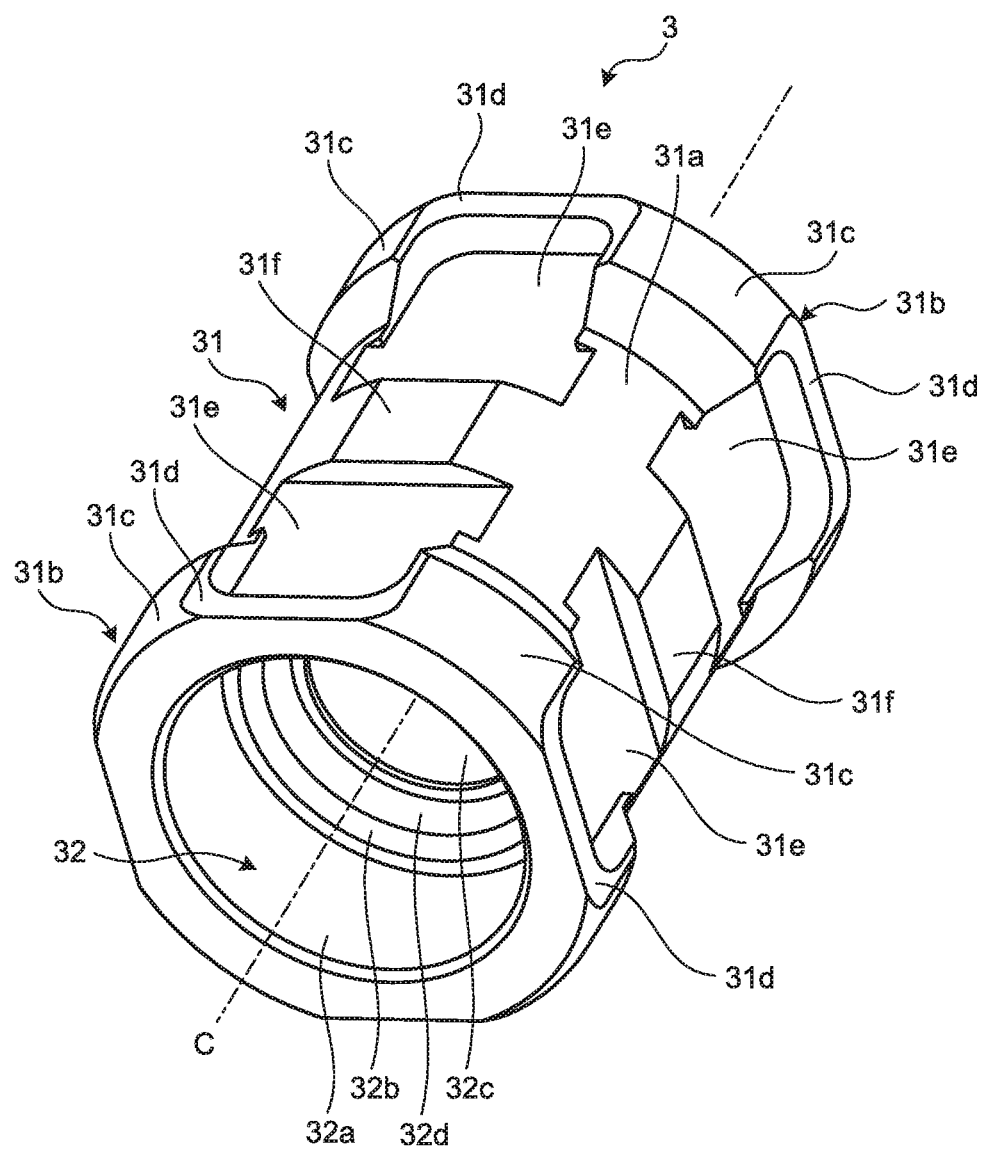
FIG. 10 is a perspective view illustrating the configuration of a moving portion in the optical unit according to the first embodiment.

FIG. 10 is a perspective view illustrating the configuration of the moving portion 3. The moving portion 3 illustrated in FIG. 10 is formed by a cylindrical shaped member having an outer circumferential portion 31 and an inner circumferential portion 32. Hereinafter, the central axis of the moving portion 3 is also referred to as the axis C. The reason for this is that the central axis of the moving portion 3 matches the central axis of the fixing portion main body 20 at the time of assembly.

The outer circumferential portion 31 includes a tube portion 31a and two flange portions 31b that are formed at each of the end portions of the tube portion 31a in the direction of the axis C and has the diameter of the outer circumference larger than that of the tube portion 31a. The tube portion 31a and the flange portions 31b may also be configured as a single member or as separate members.

Each of the flange portions 31b includes a moving-side sliding surface 31c formed of the outer circumferential surface thereof and a flat surface portion 31d formed at a part of the outer side of the flange portion 31b in the radial direction. In the case illustrated in FIG. 10, each of the flange portions 31b includes the four moving-side sliding surfaces 31c and the four flat surface portions 31d that are alternately arranged at equal spaces around the axis C along the circumferential direction. The flat surface portions 31d pass the same plane of one of the four flat surface portions 31d formed on the other end along the direction of the axis C. In other words, the outer circumferential portion 31 includes four sets of the two flat surface portions 31d that are formed at different end portions and that pass through the same associated planes.

Each of level difference portions 31e that is formed inner side of the tube portion 31a in the radial direction and that has a flat shaped outer circumferential surface is provided between four sets of the flat surface portions 31d. At the center portion of the level difference portions 31e in the axis C formed between the four sets of the flat surface portions 31d, each of notches 31f that is formed by notching the surface of the tube portion 31a and that has a flat shaped outer circumference is provided.

The inner circumferential portion 32 includes a first inner circumferential portion 32a, a second inner circumferential portion 32b, a third inner circumferential portion 32c, and an inner-circumferential-side protruding portion 32d. The diameter of the second inner circumferential portion 32b is smaller than that of the first inner circumferential portion 32a and the third inner circumferential portion 32c. Between the second inner circumferential portion 32b and the third inner circumferential portion 32c, the inner-circumferential-side protruding portion 32d that protrudes inward in the radial direction is provided.

The moving portion 3 holds the moving lens group Gv. Specifically, the second inner circumferential portion 32b in the moving portion 3 holds a first moving lens Lv1 included in the moving lens group Gv. As illustrated in FIGS. 3 and 4, it is preferable that the image side of the first moving lens Lv1 abut against the inner-circumferential-side protruding portion 32d.

The moving portion 3 is inserted into the fixing portion main body 20 while the moving-side sliding surface 31c is brought into contact with the fixing-side sliding surface 24. Furthermore, as illustrated in FIGS. 3 and 4, the moving portion 3 is inserted such that the inner side of the third inner circumferential portion 32c in the radial direction is opposite the first outer circumferential portion 51a in the rear frame portion 5. Consequently, at least a part of the image-side fixed lens group Gb is present in the inner side of the third inner circumferential portion 32c in the moving portion 3 in the radial direction. In the first embodiment, if the moving portion 3 moves to the extreme object side, at least a part of the object-side fixed lens group Gf is present in the inner side of the first inner circumferential portion 32a in the moving portion 3 in the radial direction.

The moving portion 3 having the above described configuration is formed by using, for example stainless steel, aluminum, an alloy including iron or copper, or a resin material.

In the optical unit 1, as illustrated in FIG. 4, in the direction along the axis C, a distance L1 from the position on the extreme object side of the moving-side sliding surface 31c in the moving portion 3 to the position on the extreme image side is longer than a distance L2 from an emission surface of the object-side fixed lens group Gf held by the front frame portion 4 to an incident surface of the image-side fixed lens group Gb held by the rear frame portion 5 (L1>L2). Furthermore, the distance from the position on the extreme object side of the moving-side sliding surface 31c in the moving portion 3 to the position on the extreme image side does not include a chamfer portion.

Furthermore, when the optical unit 1 is viewed from the front frame portion 4 side in the direction of the axis C, a part of the moving portion 3, a part of a coil 11, or a part of the magnet 12 is included inside the front frame portion 4.

In the following, the configuration of the voice coil motor 10 will be described. The voice coil motor 10 includes, as illustrated in FIG. 3, the coil 11 arranged in the fixing portion main body 20 in the fixing portion 2 and the magnet 12 (magnetic portion) that is arranged in the moving portion 3 such that the magnet 12 is opposite the coil 11.

The coil 11 includes, as illustrated in FIGS. 3 and 4, a first coil 11a that is wound around the outer circumference of the tube portion 21 in the fixing portion main body 20 and a second coil 11b that is arranged next to the first coil 11a in the direction of the axis C and that is wound around the outer circumference of the tube portion 21 in the fixing portion main body 20. Furthermore, the coil 11 that is previously wound may also be disposed afterward. The first coil 11a and the second coil 11b adjacent in the direction of the axis C are preferably connected in series but may also be connected in parallel.

The first coil 11a and the second coil 11b includes, as illustrated in FIGS. 3 and 4, flat surface portions 11ap and 11bp, respectively, that are opposite the lightening portion 21a in the fixing portion main body 20. Furthermore, the first coil 11a and the second coil 11b include cylindrical portions 11at and 11bt, respectively, that are opposite the tube portion 21. In the first coil 11a, the four flat surface portions 11ap and the four cylindrical portions 11at are alternately arranged on the cross section surface orthogonal to the axis C. Similarly, in the second coil 11b, the four flat surface portions 11bp and the four cylindrical portions 11bt are alternately arranged on the cross section surface orthogonal to the axis C (see FIGS. 3 and 4).

The magnet 12 includes, as illustrated in FIGS. 1 to 3, inside the flat surface portions 11ap of the first coil 11a and the flat surface portions 11bp of the second coil 11b, four prism shaped first magnets 12a and four prism shaped second magnets 12b that are opposite the flat surface portions 11ap and 11bp, respectively, and that are arranged side by side in the direction of the axis C. On the cross section surface orthogonal to the axis C, the four sets of the first magnets 12a and the second magnets 12b aligned side by side in the direction of the axis C are disposed at equal spaces of 90 degrees in the circumferential direction. A rotation regulating portion 31h is located between a set of the first magnet 12a and the second magnet 12b out of four sets. With this arrangement, it is possible to stably arrange the first magnets 12a and the second magnets 12b. Consequently, in the voice coil motor 10, a stable magnetic field is formed and thus it is possible to suppress a shake of the moving portion 3 with respect to the fixing portion 2. Furthermore, in the first embodiment, the magnets 12 are arranged at spaces of 90 degrees around the axis C; however, the magnets 12 may also be arranged at spaces of another angle.

As illustrated in FIGS. 3 and 4, the sum of the width of the first magnet 12a and the second magnet 12b in the direction of the axis C is smaller than the sum of the width of the first coil 11a and the second coil 11b in the direction of the axis C. Consequently, it is possible to always place the first magnets 12a and the second magnets 12b within the width of the first coil 11a and the second coil 11b in the direction of the axis C within the moving range of the moving portion 3.

Figure 11:
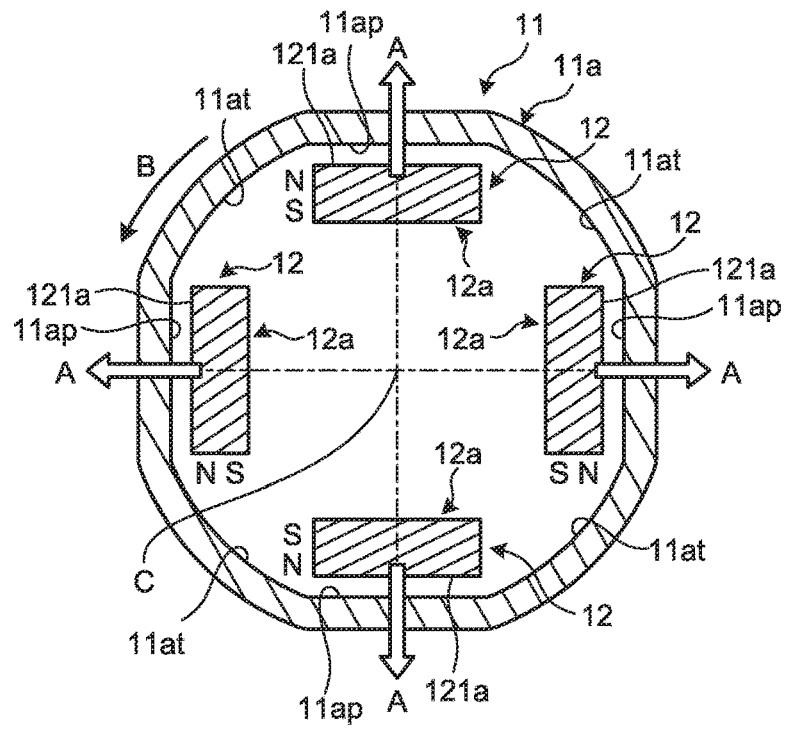
FIG. 11 is a diagram illustrating the configuration of only a voice coil motor viewed at a sectional plane taken along line IV-IV illustrated in FIG. 3.
Figure 12:
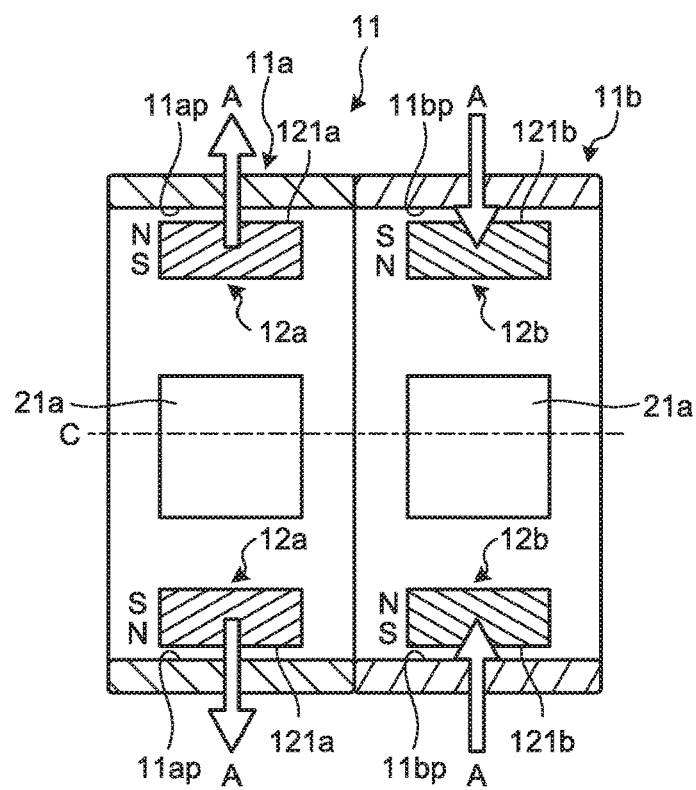
FIG. 12 is a diagram illustrating the configuration of only the voice coil motor viewed from the same cross section as that illustrated in FIG. 3.

FIG. 11 is a diagram illustrating the configuration of only the voice coil motor viewed at a sectional plane taken along line IV-IV illustrated in FIG. 3. FIG. 12 is a diagram illustrating the configuration of only the voice coil motor viewed from the same cross section as that illustrated in FIG. 3.

As illustrated in FIGS. 11 and 12, the first magnets 12a and the second magnets 12b that are paired in the direction of the axis C are separately arranged. Each of the set of the first magnets 12a and the set of the second magnets 12b is polarized in the radial direction and the magnetic poles are inversely polarized each other. In the case illustrated in FIGS. 11 and 12, it is assumed that the first magnet 12a uses the first coil 11a side as the north pole and uses the opposite side as the south pole, whereas the second magnet 12b uses the second coil 11b side as the south pole and uses the opposite side as the north pole. In this case, as indicated by white arrows A illustrated in FIGS. 11 and 12, the direction of the magnetic polarization of the first magnets 12a and the second magnets 12b is orthogonal to the axis C. Furthermore, in more generally, the direction of the magnetic polarization of the first magnets 12a and the second magnets 12b may also be the direction orthogonal to the axis C.

In the first embodiment, regarding the coil 11, it is preferable that the winding direction be inverted between the set of the first magnets 12a and the set of the second magnets 12b. For example, as illustrated in FIG. 11, if the first coil 11a is wound in the direction of an arrow B, the second coil 11b is wound in the reverse direction. Alternatively, the first coil 11a and the second coil 11b may also be connected such that the winding directions of the first coil 11a and the second coil 11b are the same and the current directions thereof are inverted. In this case, as illustrated in FIG. 11, when allowing a current to flow in the first coil 11a in the direction indicated by the arrow B, the direction of the current flowing in the second coil 11b is the direction opposite to the indicated by the arrow B.

In the optical unit 1 having the above configuration, the moving portion 3, in which each of the first magnets 12a is arranged so as to be opposite the first coil 11a, is arranged on the inner side of the fixing portion main body 20, in which the first coil 11a is wound, in the radial direction. Consequently, the flat surface portion 11ap in the first coil 11a is present in the magnetic field in the direction orthogonal to an outer surface 121a of each of the first magnets 12a in the radial direction. Furthermore, the second magnets 12b are also similarly formed. Consequently, it is possible to improve the drive efficiency and promptly move the moving portion 3. Furthermore, by allowing the outer surfaces 121a of the first magnets 12a in the radial direction and outer surfaces 121b of the second magnets 12b in the radial direction to be flat, the optical unit 1 may be easily assembled.

When applying a current to the coil 11 in the optical unit 1, the force in the direction of the axis C is generated in the moving portion 3 due to the effect of the magnetic field of the magnet 12 and then the moving portion 3 moves to the fixing portion 2 in the direction of the axis C. For example, by controlling the current that is applied to each of the first coil 11a and the second coil 11b, it is possible to allow the moving portion 3 to move to the fixing portion 2. Even in the state in which the moving portion 3 is being moved to the fixing portion 2, the outer surface of the magnet 12 in the radial direction is arranged inside the lightening portion 21a in the fixing portion main body 20.

Furthermore, in the optical unit 1, the outer circumferential surface of the flange portion 31b in the moving portion 3 forms, as illustrated in FIG. 4, the moving-side sliding surface 31c that is brought into contact with the fixing-side sliding surface 24 in the fixing portion main body 20. By making the fixing-side sliding surface 24 of the fixing portion main body 20 contact with the moving-side sliding surface 31c of the moving portion 3, it is possible to move the moving portion 3 in a state in which the moving portion 3 is always brought into contact with the fixing portion main body 20 and it is possible to suppress the inclination of the moving portion 3 with respect to the fixing portion 2, whereby it is possible to accurately move the moving portion 3.

In the following, a description will be given of an attraction force generated between the magnet 12 and peripheral members of the magnet 12 and the material property of the fixing portion 2. A small attraction force is generated, due to magnetism, between the magnet 12 and the fixing portion 2 (the fixing portion main body 20, the front frame portion 4 and/or the rear frame portion 5) and the attraction force may sometimes cause a hindrance of a reduction in size or stopping accuracy. In a case of the optical unit 1 that uses the voice coil motor 10 with the moving magnet (MM) type according to the first embodiment, the attraction force in the driving direction (in the direction of the axis C) and the friction force caused by the attraction force in the direction orthogonal to the driving direction act as a hindrance. In particular, if the size of the optical unit 1 is reduced, because the distance between the magnet 12 and the fixing portion 2 is decreased, the magnitude of the attraction force is increased. Consequently, when reducing the size of the optical unit 1, because the ratio of the attraction force with respect to the driving force becomes worse, the size of the optical unit 1 is consequently increased due to designing the attraction force and the driving force that exceeds the friction force due to the attraction force.

For example, when disposing the optical unit 1 in an endoscope, the diameter of a common endoscope is about 9.0 mm and, in the endoscope, an optical unit, a plurality of light guides, a forceps channel, an air/water pipe, a spray channel, and the like are arranged; therefore, the diameter allowed to be used for the optical unit 1 is about 4.0 mm. Furthermore, because operability of the endoscope is increased as the length of the hard portion of a distal end is decreased, it is preferable that the total length of the optical unit 1 in the optical axis direction be about 10 mm. Furthermore, let alone, in a case of an endoscope having further smaller diameter, such as a nasal endoscope, the size of an optical unit needs to be further reduced. Furthermore, in an endoscope, because the diameter is extremely important, regarding the optical unit 1, the diameter of about 4.0 mm needs to be more reduced by only 0.05 mm.

Here, in a case of the optical unit 1 that uses the voice coil motor 10 with the MM type such as that described in the first embodiment, lenses, the fixing portion 2, the moving portion 3, the coil 11, the magnet 12, and the like are arranged in the space with about the diameter of 4.0 mm and the total length of 10 mm; therefore, the distance between the magnet 12 and the fixing portion 2 is extremely short. Furthermore, if the fixing portion 2 is formed by a magnetism substance, the attraction force generated between the fixing portion 2 and the magnet 12 is increased in proportion to the square of the distance.

In the voice coil motor 10 in the optical unit 1 arranged in an endoscope, due to an increase in the attraction force and a decrease in the driving force due to a reduction in the size, the effect of the attraction force is relatively increased. Because the driving force of the voice coil motor 10 needs to overcome drag (force that opposes the driving force) due to the attraction force, if drag due to the attraction force is greater than the driving force, the driving force needs to be increased by that amount and the size of the magnets and coils needs to be increased. For example, if drag due to the attraction force corresponds to an amount of 20% of the driving force, a countermeasure is taken by, for example, increasing the thickness of the magnet 12 and increasing the magnetic force by 20% and, thus, the diameter of the optical unit 1 is increased.

Consequently, from among the members in the fixing portion 2, the member whose distance from the magnet 12 is small and that is affected by the attraction force is preferably formed by using a non-magnetic material. If so, it is possible to ideally make the attraction force between the magnet 12 and the member zero. As a non-magnetic material, for example, a metallic material, such as austenitic stainless steel, aluminum, titanium, copper, copper alloy, or a resin material, such as polyether ether ketone (PEEK), polyacetal, polycarbonate, and polyimide, may be used.

Here, the member in the optical unit 1 disposed in an endoscope needs to decrease the thickness due to a reduction in the size of the optical unit (rough standard of about 0.1 mm). Consequently, a metallic material having high rigidity and workability is suitable and, as the material that forms the member of the optical unit 1, austenitic stainless steel is preferably used.

However, austenitic stainless steel is generally nonmagnetic but has a slight magnetic property due to processing. Furthermore, even if processing is not performed, austenitic stainless steel has a faint magnetic property (about relative permeability of 1.003 to 1.005) enough to usually be ignored.

Figure 13:
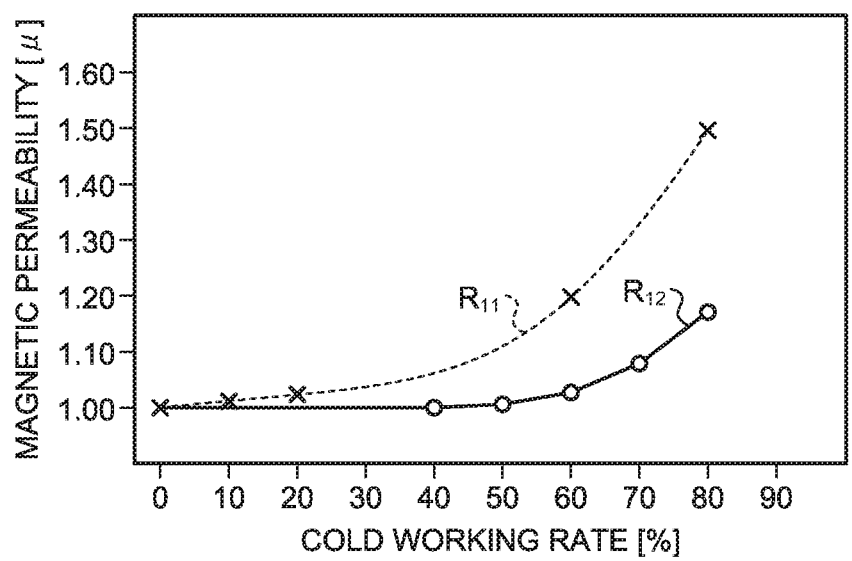
FIG. 13 is a diagram illustrating magnetic permeability of austenitic stainless steel after cold working has been performed.

FIG. 13 is a diagram illustrating magnetic permeability of austenitic stainless steel after cold working and is a graph indicating the relationship between the cold working rate and magnetic permeability. In FIG. 13, the magnetic permeability with respect to the cold working rate of SUS304 is represented by a curve $R_{11}$ and the magnetic permeability with respect to the cold working rate of SUS305 is represented by a curve $R_{12}$. Furthermore, the cold working rate $((A_0 - A_1)/A_0 \times 100)$ is the ratio of a difference $(A_0 - A_1)$ between a cross-sectional area $(A_0)$ of a material before processing and a cross-sectional area $(A_1)$ of the material after processing to the cross-sectional area of the material before processing. As illustrated in FIG. 13, by performing cold working on the austenitic stainless steel, it is possible to confirm an increase, in accordance with an increase in the cold working rate, in magnetic permeability in both the austenitic stainless steel materials of SUS304 and SUS305. Consequently, an attraction force is generated between the austenitic stainless steel material and the magnet.

In contrast, by performing solution treatment processing (magnetic annealing processing) after the processing, the austenitic stainless steel may remove the magnetism generated due to the processing. If solution treatment processing is performed after the processing, austenitic stainless steel may be used as a non-magnetic material suitable for the optical unit 1 in an endoscope.

As described above, regarding the optical unit 1 disposed in the endoscope, if the diameter of the optical unit 1 is decreased to 4.0 mm or less and the total length thereof is decreased to 10 mm or less, in order to arrange members, such as the lenses, the fixing portion 2, the moving portion 3, the coil 11, and the magnet 12, the moving portion 3 needs to be formed with the diameter of about 3 mm or less, the inner diameter ϕ of 2.8 mm or less, and the total length of 4.0 mm or less. At this time, the weight in the case where the material property of the moving portion 3 is austenitic stainless steel is about 28 mg and the weight in the case where the material property is aluminum is about 9.0 mg. Furthermore, if the magnet 12 is formed by a neodymium magnet having the size of 1.0×1.0×0.5 (mm), the weight thereof becomes about 3.0 mg/piece. Consequently, although a variation is generated based on the material property of the moving portion 3 and the number of the magnets 12 (the total number of the first magnets 12a and the second magnets 12b), in order to implement the optical unit 1 to be disposed in the endoscope by using the voice coil motor 10 with the MM type, the total weight of the moving portion 3 becomes about 20 mg to 100 mg. Thus, the driving force of the voice coil motor 10 in the optical unit 1 having this configuration needs to be about 40 mgf to 1000 mgf by considering the weight of the moving portion 3 and the factor of safety (2 to 10); otherwise, it is not possible to implement the optical unit 1 that may be disposed in the endoscope. Here, the factor of safety is a value obtained by dividing a designed driving force by a limit driving force (value taking into consideration of the weight of the moving portion 3, drag due to an attraction force, or the like) in which the moving portion 3 is not able to be driven and indicates the designed driving force is sufficient as the value is larger.

Figure 14:
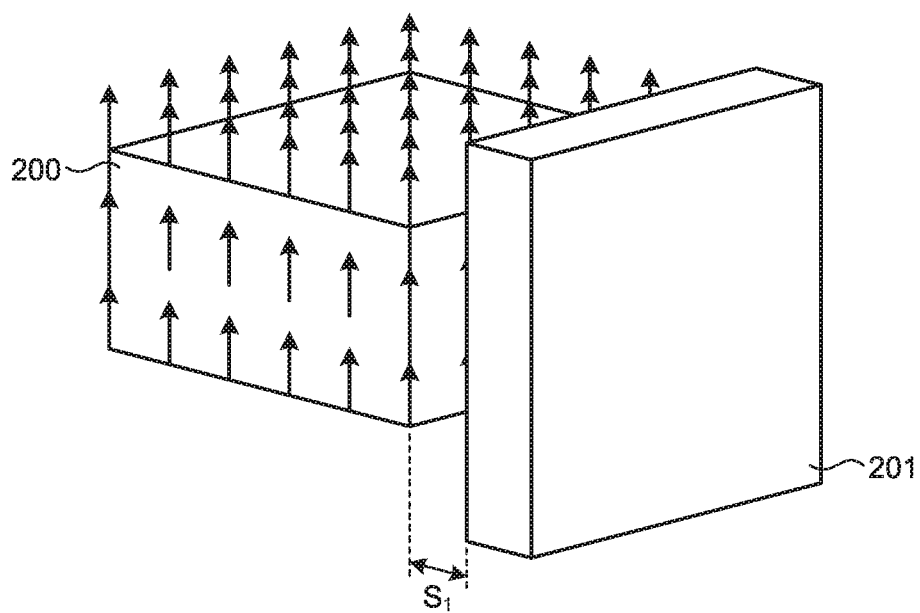
FIG. 14 is a diagram illustrating arrangement when an attraction force is applied to a member in the direction orthogonal to the magnetization direction of a magnet.
Figure 15:
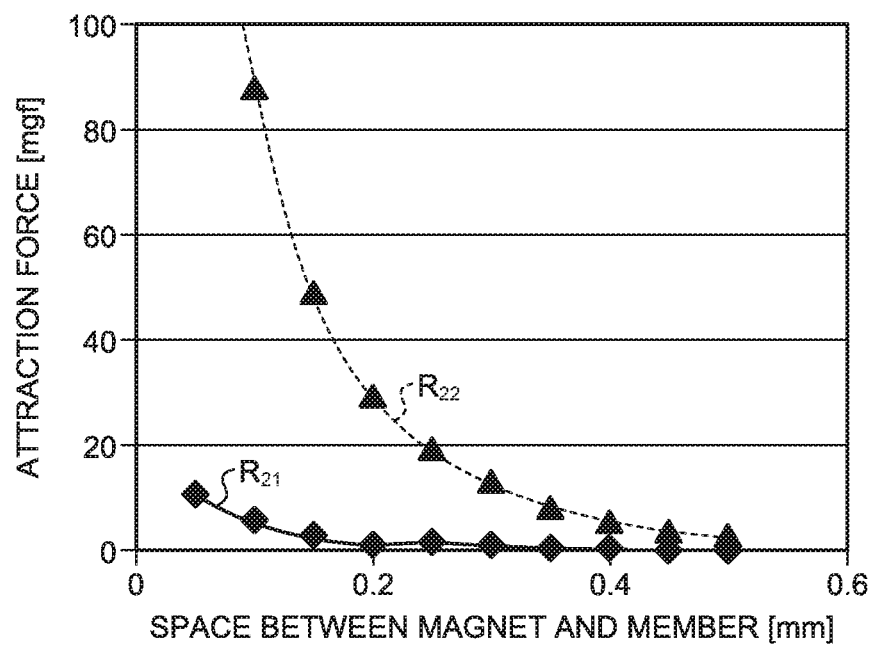
FIG. 15 is a graph illustrating the relationship between a space between the magnet and the member and an attraction force that is applied to the member and that is in the direction orthogonal to the magnetization direction of the magnet.

Here, a description will be given of an attraction force of the magnet with the size of 1.0×1.0×0.5 (mm) that is appropriate for the magnet 12 of the voice coil motor 10 in an optical unit in an endoscope. FIG. 14 is a diagram illustrating arrangement when an attraction force is applied to a member in a direction orthogonal to the magnetization direction of a magnet. FIG. 15 is a graph illustrating the relationship between a space between the magnet and the member and the attraction force that is applied to the member and that is in the direction orthogonal to the magnetization direction of the magnet. Furthermore, in the first embodiment, the direction orthogonal to the magnetization direction of the magnet corresponds to the direction of the optical axis (direction of the axis C). Furthermore, the space between the magnet and the member corresponds to a space $S_1$ between a magnet 200 and a member 201 illustrated in FIG. 14.

Figure 16:
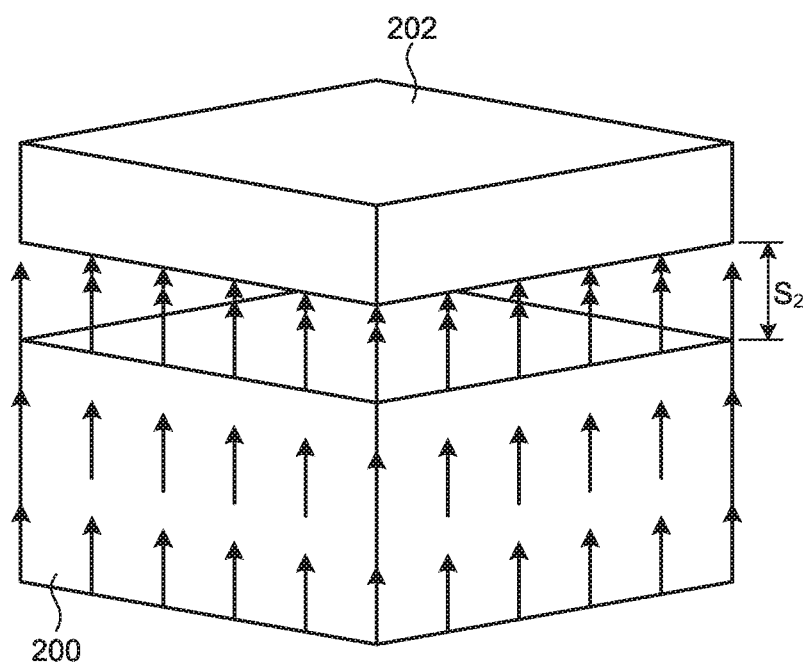
FIG. 16 is a diagram illustrating arrangement when an attraction force of the magnet in the magnetization direction is applied to the member.
Figure 17:
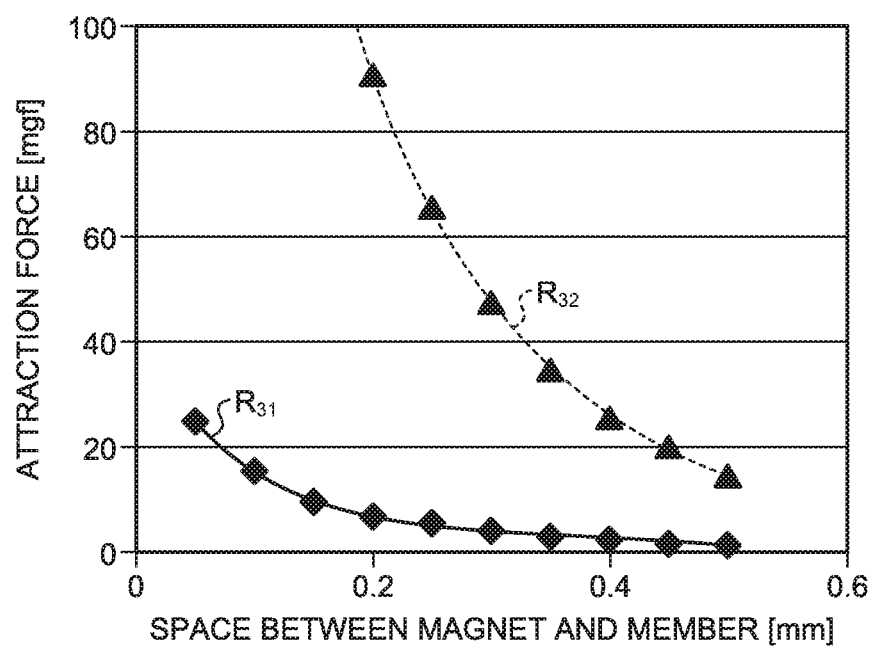
FIG. 17 is a graph illustrating the relationship between a space between the magnet and the member and an attraction force that is applied to the member and that is in the magnetization direction of the magnet.

FIG. 16 is a diagram illustrating arrangement when an attraction force of the magnet in the magnetization direction is applied to the member. FIG. 17 is a graph illustrating the relationship between a space between the magnet and the member and the attraction force that is applied to the member and that is in the magnetization direction of the magnet. Furthermore, the space between the magnet and the member corresponds to a space $S_2$ between the magnet 200 and a member 202 illustrated in FIG. 16.

In FIGS. 15 and 17, curves $R_{21}$ and $R_{31}$ indicate the relationship, regarding the member (relative permeability of 1.040) formed by ideal austenitic stainless steel, between the space between the magnet and the member and the attraction force of the magnet in the direction orthogonal to the magnetization direction. Furthermore, curves $R_{22}$ and $R_{32}$ indicate the relationship, regarding the member (relative permeability of 1.050) formed by austenitic stainless steel that has been processed and that has a magnetic property, between the space between the magnet and the member and the attraction force of the magnet in the direction orthogonal to the magnetization direction. Furthermore, a neodymium magnet with the size of 1.0×1.0×0.5 (mm) is used for the magnet 200 and SUS303 with the size of 1.0×1.0×0.2 (mm) is used for the members 201 and 202.

As illustrated in FIGS. 15 and 17, both attraction forces are decreased as the spaces between the magnets and the members are increased. Furthermore, the member (relative permeability of 1.050) formed by austenitic stainless steel that has a magnetic property due to being processed has the attraction force larger than that of the member (relative permeability of 1.040) formed by ideal austenitic stainless steel.

The attraction force indicated above is for each magnet; however, because eight magnets are used in the first embodiment, in the direction orthogonal to the magnetization direction of the magnets, as an approximate maximum value that is possibly generated, the attraction force that is four times the simulation result described above and that corresponds to four magnets located at the same positions in the optical axis direction is generated. Furthermore, also regarding the attraction force of the magnets in the magnetization direction, as an approximate maximum value that is possibly generated, the attraction force of 4 (factor)/1.4√2–2.83 (factor) is generated as the resultant force of the attraction force of the four magnets that are present in two columns on one side of the optical axis. Furthermore, as the drag due to the attraction force in the magnetization direction, by multiplying 0.5 that is a coefficient friction by the obtained resultant force, the drag due to the attraction force that is 1.41 times the simulation result is generated.

Figure 18:
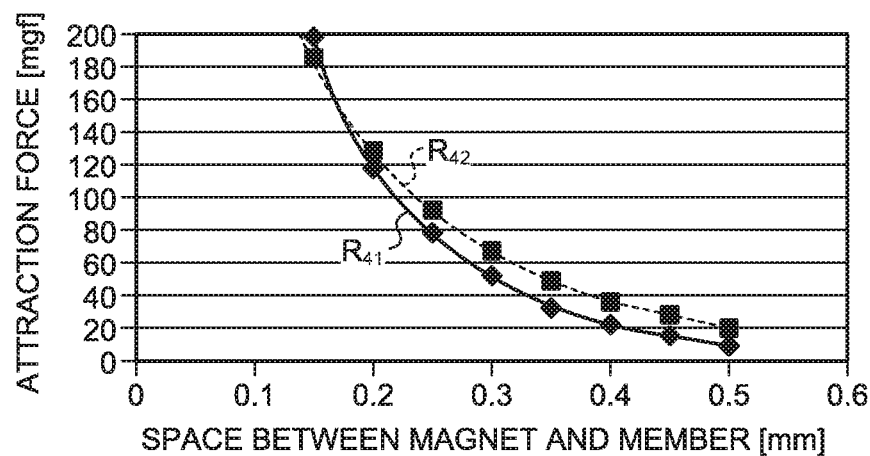
FIG. 18 is a graph illustrating the result obtained by simulating the relationship, when using a member having relative permeability of 1.050 and eight magnets, between a space between a magnet and a member and an attraction force that is applied to the member in the direction orthogonal to the magnetization direction of the magnet.

FIG. 18 is a graph illustrating the result obtained by simulating the relationship, when using a member having relative permeability of 1.050 (value of processed austenitic stainless steel) and eight magnets, between a space between a magnet and a member and an attraction force that is applied to the member in the direction orthogonal to the magnetization direction of the magnet. In FIG. 18, a curve $R_{41}$ indicates the result obtained by multiplying the attraction force in the direction orthogonal to the magnetization direction by four and a curve $R_{42}$ indicates the result obtained by multiplying the attraction force in the magnetization direction by 1.41. As described above, the driving force of the voice coil motor in the optical unit 1 according to the first embodiment is about 40 mgf to 1000 mgf. Considerably large drag due to attraction force is generated with respect to the driving force.

Because the driving force of the voice coil motor 10 needs to overcome drag (force that opposes the driving force) due to the attraction force, a decrease in attraction force is a major issue for a size reduction of the optical unit 1. For example, as described above, if the drag due to the attraction force corresponds to 20% of the driving force, the driving force needs to be increased by 20% due to the attraction force. Thus, if the thickness of the magnet with the size of 1.0×1.0×0.5 (mm) is increased and a total amount of magnetic flux is attempted to be increased by 20%, the thickness of the magnet becomes about 0.72 mm. Consequently, with the configuration in the first embodiment, the diameter of the optical unit 1 is greater by about 0.44 mm and thus the size thereof is increased by about 11% than the optical unit with the diameter of 4.0 mm. Therefore, the size is increased unless the attraction force is decreased to a certain level or low with respect to the weight of the moving portion 3.

Here, as described in the first embodiment, if the moving portion 3 has the diameter of 3 mm, the inner diameter ϕ of 2.8 mm, and the total length of 4.0 mm and the material property of the moving portion 3 is austenitic stainless steel, the weight of the moving portion 3 becomes about 28 mg. The weight of eight magnets becomes about 24 mg and the weight of the moving portion 3 becomes about 52 mg. If the factor of safety of the driving force is assumed to be 2, the driving force is about 104 mgf. If it is assumed that rough standard of not resulting in an increase in size is that the drag due to the attraction force is equal to or less than 20% of the driving force, the drag due to the attraction force needs to be equal to or less than about 21 mgf. Consequently, the member in which the drag due to the attraction force is equal to or less than about 21 mgf and the distance (space) from the magnet is equal to or less than about 0.5 mm needs to be a non-magnetic member. Furthermore, nonmagnetic mentioned here indicates that at least the relative permeability is less than 1.050 and is, more desirably, less than 1.010.

In the first embodiment, a non-magnetic material is used as the material property of the member, from among the fixing portion main body 20, the front frame portion 4, and the rear frame portion 5 constituting the fixing portion 2, that has the minimum distance from the magnet 12, i.e., that has the above described distance (space), that is smaller than the space that does not result in an increase in size. The minimum distance mentioned here is the minimum distance between the magnet 12 and each of the members and is the closest distance when the moving portion 3 moves. In the first embodiment, because the fixing portion main body 20 that holds therein the moving portion 3 is the closest to the magnet 12 and the above described space is equal to or less than the distance that results in an increase in size, the fixing portion main body 20 is formed by at least using a non-magnetic material. Furthermore, between the front frame portion 4 and the rear frame portion 5, the frame portion having a smaller minimum distance with the magnet 12 may also be formed by using a non-magnetic material or, alternatively, the front frame portion 4 and the rear frame portion 5 may also be formed by using a non-magnetic material. Furthermore, depending on the configuration, in some cases, the minimum distance of the fixing portion main body 20 is greater than that of the front frame portion 4 and the rear frame portion 5. In this case, from among the fixing portion main body 20, the front frame portion 4, and the rear frame portion 5, the member having the distance (space) of 0.5 mm or less with the magnet is formed by using a non-magnetic material.

Furthermore, a copper alloy and copper are also non-magnetic materials, may be used for a material that forms the member of the optical unit 1, and are suitable for reducing the size of the member. If a copper alloy or copper is used, it is desirable to use a plated material that has a nonmagnetic property and that has suitable workability for plating. Because it is difficult to perform electrolytic plating on a small sized metallic material, electroless plating is preferable. An example of electroless and nonmagnetic plating, electroless nickel plating with, high phosphorus content, for example, the content rate of phosphorus equal to or greater than 5.0% may be used. By performing electroless nickel plating on a metallic material, such as a copper alloy, or copper, having high phosphorus content, it is possible to use as the non-magnetic material suitable for the optical unit 1 in an endoscope.

Then, by forming the moving portion 3 using a non-magnetic material, it is possible to reduce the attraction force between the moving portion 3 in which the magnet 12 is fixed and the members, i.e., the fixing portion main body 20, the front frame portion 4, and the rear frame portion 5. Because the moving portion 3 may be formed by using the above described non-magnetic material, and the driving force may be reduced if the weight is decreased, whereby it is possible to use aluminum that has relatively high rigidity and is suitable for workability.

According to the first embodiment described above, a non-magnetic material is used as the material property of the member, from among the fixing portion main body 20, the front frame portion 4, and the rear frame portion 5 constituting the fixing portion 2, that has the minimum distance from the magnet 12, i.e., that has the space smaller than the space in which the size of the optical unit 1 is not increased when the driving force is calculated by considering the attraction force, it is possible to secure operational stability of stable operation free from the attraction force while maintaining a reduction in size and weight of the actuator that moves the moving lens forward and backward.

Furthermore, according to the first embodiment, because the magnet 12 is disposed at each of the level difference portions 31e having a concave shape in the moving portion 3, it is possible to implement a reduction in the size in the direction in which the two sets of the magnets 12 are opposite.

Furthermore, according to the first embodiment, by configuring the fixing portion 2 by using the fixing portion main body 20, the front frame portion 4, and the rear frame portion 5, it is possible to reduce the number of parts and assembly steps and also possible to increase the design flexibility, thus implementing a reduction in cost.

Furthermore, according to the first embodiment, in the optical unit 1, in the direction along the axis C, because the distance L1 from the position on the extreme object side on the moving-side sliding surface 31c of the moving portion 3 to the position on the extreme image side is longer than the distance L2 from the emission surface of the object-side fixed lens group Gf held by the front frame portion 4 to the incident surface of the image-side fixed lens group Gb held by the rear frame portion 5, it is possible to suppress the inclination of the moving portion 3 with respect to the fixing portion 2. Consequently, it is possible to stably drive the optical unit 1 and also possible to implement a reduction in size in the direction of the axis.

Furthermore, according to the first embodiment, because the coil 11 is wound around the axis C, a sliding axis of the moving portion 3 and an action axis of a propulsion force generated by the voice coil motor 10 may be made the same and thus stable driving is possible.

Furthermore, according to the first embodiment, because the fixing-side sliding surface 24 of the fixing portion 2 is formed by being divided in the circumferential direction, it is possible to reduce in the size of the optical unit 1 with simple structure.

Furthermore, according to the first embodiment, the fixing portion main body 20 has a shape of being divided along the circumferential direction at one end in the direction of the axis C and holds the front frame portion 4. Consequently, it is possible to increase the rigidity of the fixing portion 2 without increasing the size in the radial direction. Furthermore, by holding one end of the fixing portion main body 20 is held by being brought into contact with the front frame portion 4, the shape of the end portion that is on the side different from the side linked to the tube portion 21 in the object-side thick portion 22 is fixed, thus stabilizing the shape of the fixing-side sliding surface 24. Consequently, the optical unit 1 may be stably driven and it is possible to implement a reduction in the size in the radial direction.

Furthermore, according to the first embodiment, because a plurality of the magnets 12 is symmetrically arranged around the axis C, it is possible to stably increase the driving force.

Furthermore, according to the first embodiment, the magnet 12 includes a plurality sets of the first magnets 12a and the second magnets 12b that are adjacent in the direction of the axis C and that have opposite magnetic polarization directions; the plurality of the first magnets 12a have the same magnetic polarization direction; the coil 11 includes the first coil 11a that is opposite the plurality of the first magnets 12a and the second coil 11b that is opposite the plurality of the second magnets 12b and that is connected to the first coil 11a; and the directions of the current flowing in the first coil 11a and the second coil 11b are opposite. Consequently, it is possible to increase the driving force.

First Modification of First Embodiment

Figure 19:
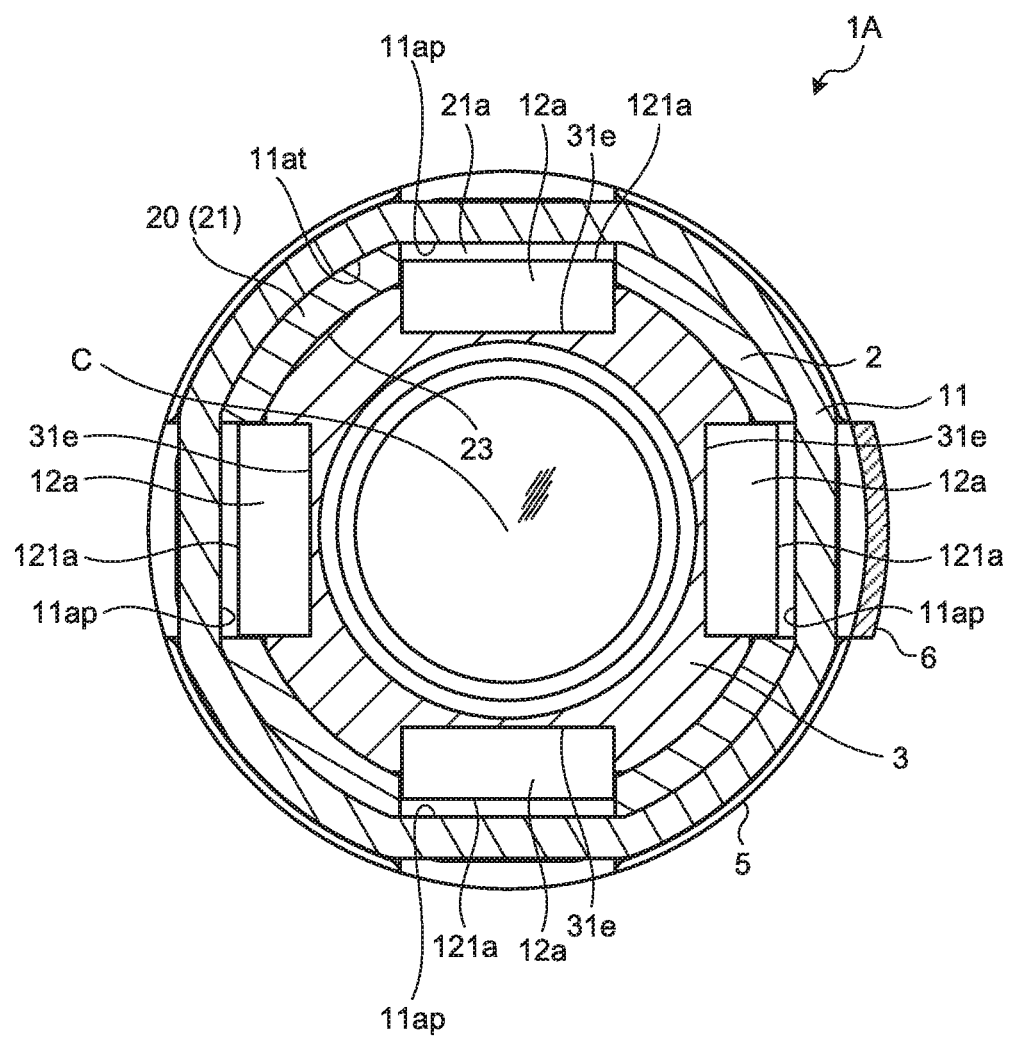
FIG. 19 is a sectional view illustrating the configuration of a relevant part in an optical unit according to a first modification of the first embodiment.

FIG. 19 is a sectional view illustrating the configuration of a relevant part in an optical unit according to a first modification of the first embodiment and is a diagram associated with a cross section of the optical unit viewed at a sectional plane taken along line I-I illustrated in FIG. 3. An optical unit 1A illustrated in FIG. 19 includes the fixing portion 2, the moving portion 3 capable of moving with respect to the fixing portion 2, the voice coil motor 10 (see FIG. 1, etc.) that generates a driving force that moves the moving portion 3 with respect to the fixing portion 2, and a biasing member 6 that biases, by attracting the moving portion 3 to the fixing portion 2 side, the moving portion 3 in the direction in which the moving portion 3 approaches the fixing portion 2.

The biasing member 6 has a band shape formed by using a ferromagnetic substance member and attracts the moving portion 3 to the fixing portion main body 20 side. As the ferromagnetic substance, iron, nickel, cobalt, or an alloy mainly made of iron and nickel or cobalt may be used. In the first modification, it is assumed that the biasing member 6 extends in the direction of the axis C. One end of the biasing member 6 in the longitudinal direction is fixed on the side surface of the front frame portion 4 and the other end of the biasing member 6 is fixed to the side surface of the fixing portion main body 20.

In the optical unit 1A, the attraction force due to magnetism acts between the biasing member 6 and the magnet 12 and the magnet 12 is attracted to the biasing member 6 side. Consequently, it is possible to adjust the position of the moving portion 3 that is in the fixing portion main body 20 and that is on the plane orthogonal to the direction of the axis C and it is possible to suppress a shift of the position of the moving portion 3 on the subject plane. Furthermore, in the first modification, the biasing member 6 is arranged at the substantially center of the optical unit 1 in the first direction and the longitudinal direction is arranged in the direction of the axis C; however, the configuration is not limited thereto.

In this way, by providing the biasing member 6 having a function of backlash gathering, the moving portion 3 (moving lens) may be driven with high positional accuracy. Consequently, the degree of freedom of optical design is increased, thus enabling a design suitable for a reduction in size. In contrast, the biasing force of backlash gathering needs to be designed such that the biasing force always exceeds the sum of the gravity and the attraction force that is generated in the backlash gathering. Thus, if the attraction force is present, the biasing force of the backlash gathering is increased and the friction force due to the biasing force is also increased. Because the driving force also needs to overcome the friction force due to the biasing force, the size of the optical unit is increased. Consequently, when the member has the function of backlash gathering, by forming a member, such as the fixing portion 2, by using a non-magnetic material and decreasing the attraction force, it is possible to reduce the size of the optical unit 1 to the size so as to be capable of being arranged in an endoscope.

According to the first modification described above, because an attraction force due to magnetism is applied between the biasing member 6 and the magnet 12 formed of magnetic materials and the magnet 12 is attracted to the biasing member 6 side, by suppressing a deviation of the position of the moving portion 3 that is in the fixing portion main body 20 and that is on the plane orthogonal to the direction of the axis C, it is possible to suppress the inclination of the moving portion 3 with respect to the fixing portion main body 20, thus improving driving stability. Furthermore, by fixing the position of the moving portion 3 in the fixing portion main body 20, it is possible to suppress eccentricity of the optical system and the degradation of the performance due to eccentricity.

In the following, second to fifth modifications of the first embodiment will be described. In the first embodiment described above, a case in which each of the first magnets 12a and the second magnets 12b has a prism shape; however, the shape thereof is not limited to this.

Second Modification of First Embodiment

Figure 20:
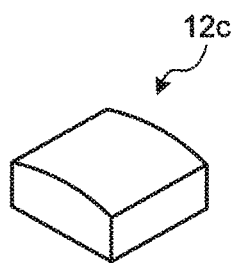
FIG. 20 is a perspective view illustrating the configuration of a relevant part in an optical unit according to a second modification of the first embodiment.

FIG. 20 is a schematic view illustrating the configuration of a relevant part in an optical unit according to a second modification of the first embodiment and a perspective view illustrating the configuration of a magnet of a voice coil motor. As a magnet 12c according to the second modification, a portion having a curved surface used for the outer circumferential surface may also be included.

Third Modification of First Embodiment

Figure 21:
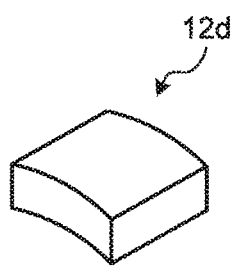
FIG. 21 is a perspective view illustrating the configuration of a relevant part in an optical unit according to a third modification of the first embodiment.

FIG. 21 is a schematic view illustrating the configuration of a relevant part in an optical unit according to a third modification of the first embodiment and a perspective view illustrating the configuration of a magnet of the voice coil motor. As a magnet 12d according to the third modification, the surfaces opposite in the outer circumferential surface may also have arch shape that forms a curved surface.

Fourth Modification of First Embodiment

Figure 22:
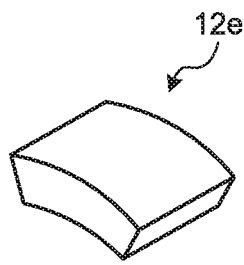
FIG. 22 is a perspective view illustrating the configuration of a relevant part in an optical unit according to a fourth modification of the first embodiment.

FIG. 22 is a schematic view illustrating the configuration of a relevant part in an optical unit according to a fourth modification of the first embodiment and a perspective view illustrating the configuration of the magnet in the voice coil motor. As a magnet 12e according to the fourth modification, the opposite surfaces of the outer circumferential surface may also have arch shape that forms a curved surface and have different length in the direction extending in the arch shape.

Fifth Modification of First Embodiment

Figure 23:
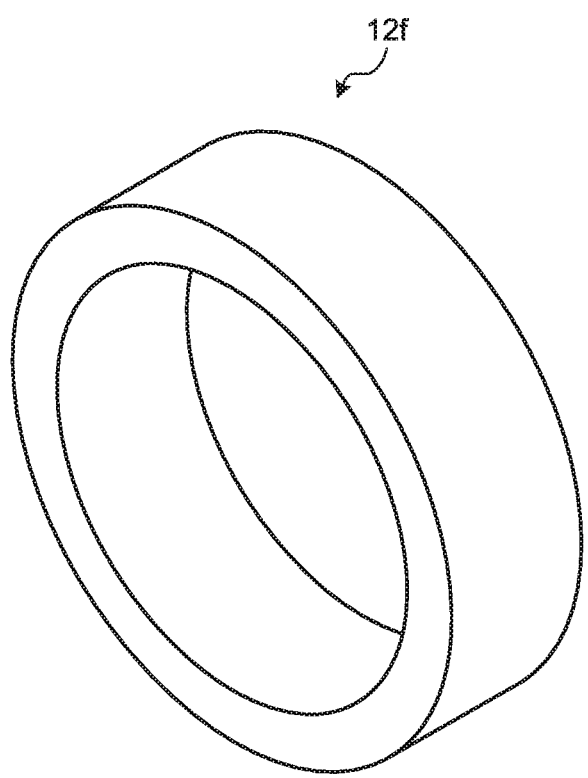
FIG. 23 is a perspective view illustrating the configuration of a relevant part in an optical unit according to a fifth modification of the first embodiment.

FIG. 23 is a schematic view illustrating the configuration of a relevant part in an optical unit according to a fifth modification of the first embodiment and a perspective view illustrating the configuration of a magnet in the voice coil motor. As a magnet 12f according to the fifth modification, the moving portion 3 may also have a ring shape capable of revolving.

Second Embodiment

Figure 24:
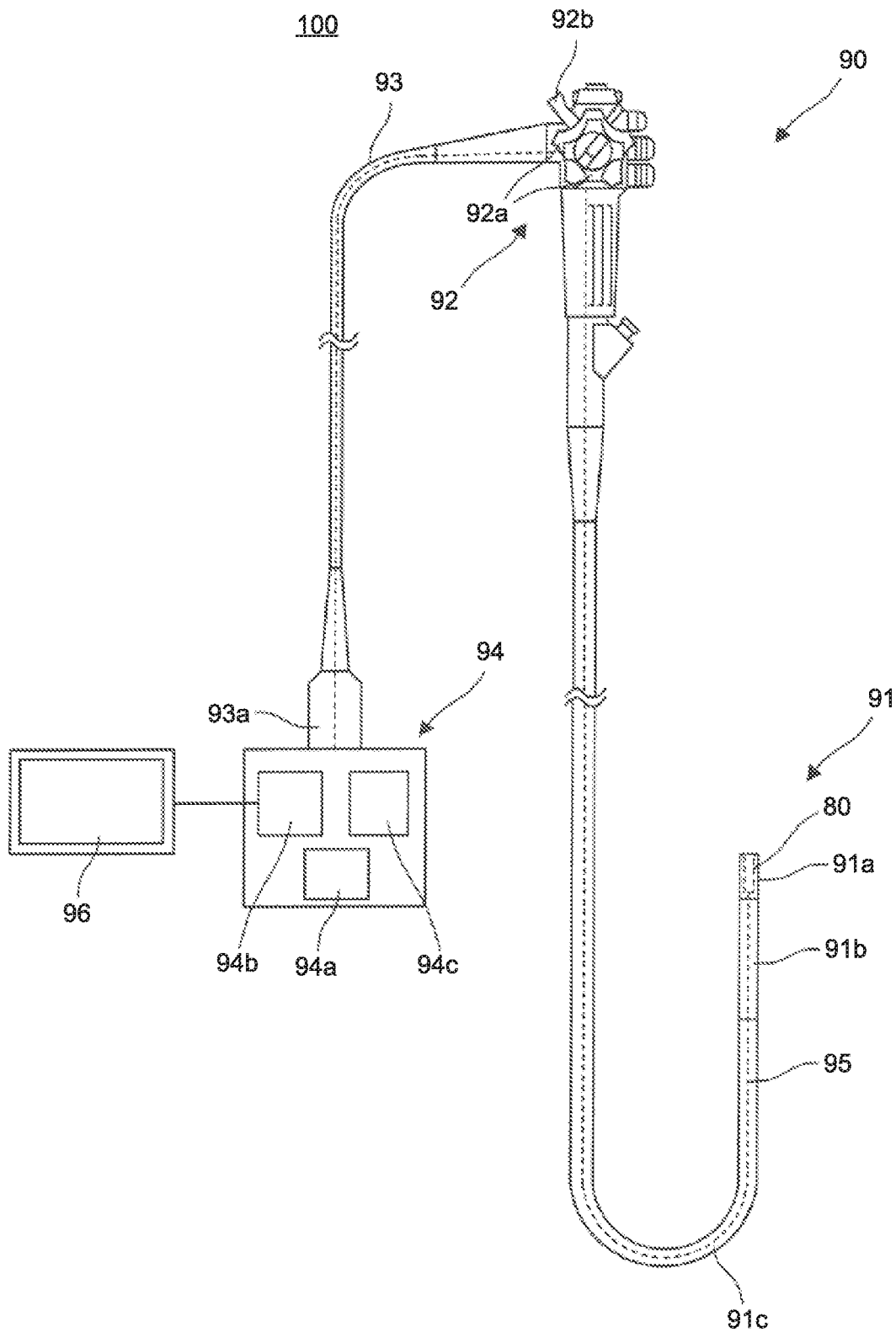
FIG. 24 is a diagram illustrating the configuration of an endoscope system provided with an endoscope according to a second embodiment.

FIG. 24 is a diagram illustrating the configuration of an endoscope system provided with an endoscope according to a second embodiment. An endoscope system 100 illustrated in FIG. 24 includes an endoscope 90, a control device 94, and a display device 96. The endoscope 90 includes the optical units 1 and 1A according to the first embodiment and the modifications described above. In the second embodiment, a description will be given with the assumption that, for example, the optical unit 1 according to the first embodiment is included.

The endoscope 90 may be introduced into a subject, such as a human body, and optically captures a predetermined observed region inside the subject. Furthermore, the subject in which the endoscope 90 is introduced is not limited to a human body and another living body or an artificial material, such as a machine or a building, may also be used. In other words, the endoscope 90 may also be a medical endoscope or an industrial endoscope.

The endoscope 90 includes an insertion portion 91 that is introduced into a subject, an operating unit 92 located at the proximal end of the insertion portion 91, and a universal code 93 as a composite cable extending from the operating unit 92.

The insertion portion 91 includes a distal end portion 91a disposed at the distal end, a curved section 91b that is freely bendable and is disposed on the proximal end side of the distal end portion 91a, and a flexible tube 91c that is disposed on the proximal end side of the curved section 91b, that is connected to the distal end side of the operating unit 92, and that has flexibility. At the distal end portion 91a, an imaging unit 80 that condenses light from an object of shooting and that captures the object of shooting is provided. The imaging unit 80 includes the optical unit 1 that condenses light from the object of shooting and an image sensor that photoelectrically converts the light condensed by the optical unit 1 and that outputs the light. The image sensor is formed by using CCD or CMOS. Furthermore, the endoscope 90 may also be a rigid endoscope that does not have the flexible tube 91c in the insertion portion 91.

The operating unit 92 includes an angle operating unit 92a that operates a curved state of the curved section 91b and a zoom operating unit 92b that designates the operation of the voice coil motor 10 described above and that performs zoom operation in the optical unit 1. The angle operating unit 92a is formed in a knob shape and the zoom operating unit 92b is formed in a lever shape; however, the operating units may also be another type, such as a volume switch or a push switch.

The universal code 93 is a member that connects the operating unit 92 and the control device 94. The endoscope 90 is connected to the control device 94 via a connector 93a disposed at the proximal end portion of the universal code 93.

In the insertion portion 91, the operating unit 92, and the universal code 93, a cable 95, such as a wire, an electrical wire, or an optical fiber, is inserted.

The control device 94 includes a drive control unit 94a that controls the curved state of the curved section 91b, an image control unit 94b that controls the imaging unit 80, and a light source control unit 94c that controls a light source device (not illustrated). The control device 94 includes a processor, such as a central processing unit (CPU), and performs overall control of the endoscope system 100.

The drive control unit 94a includes an actuator and is mechanically connected to the operating unit 92 and the curved section 91b via the wire. The drive control unit 94a controls the curved state of the curved section 91b by moving forward and backward the wire.

The image control unit 94b is electrically connected to the imaging unit 80 and the operating unit 92 via the electrical wire. The image control unit 94b performs drive control of voice coil motor 10 included in the imaging unit 80 and performs a process on an image captured by the imaging unit 80. The image processed by the image control unit 94b is displayed by the display device 96.

The light source control unit 94c is optically connected to a light source and the operating unit 92 by the optical fiber. The light source control unit 94c controls the brightness of the light source irradiated from the distal end portion 91a.

Furthermore, it may also be possible to configure the operating unit 92 such that the operating unit 92 is formed as a separate unit from the insertion portion 91 and perform the operation of the insertion portion 91 by remote control.

Because the endoscope system 100 having the configuration described above includes the imaging unit 80 including the optical unit 1 described above, the size is small and a prompt change in zoom is possible. Consequently, the endoscope system 100 is appropriate for capturing a moving image.

Furthermore, with the endoscope system 100, because the magnet 12 is arranged in the moving portion 3, whereas, the coil 11 is arranged in the fixing portion 2, the cable connected to the coil 11 does not need to be moved. Consequently, there is no possibility of disconnection due to a move of a cable in limited space in the distal end portion 91a in the endoscope 90, thus also having excellent durability.

Other Embodiments

In the above, modes for carrying out the present disclosure has been described, the present disclosure is not limited to only the embodiments described above. For example, the optical unit 1 described above may also further include at least one magnetic detector that detects magnetism and a current control unit that controls current flowing in the coil 11 based on the detection result obtained by the magnetic detector. The magnetic detector is implemented by using, for example, a Hall effect element or magneto resistance effect element (MR element). The magnetic detector is secured in a supporting member provided on the outer circumferential side of the coil 11 in the radial direction. By controlling the current flowing in the coil 11 based on the magnetism detected by the magnetic detector, it is possible to more accurately control a driving speed and a stop position of the moving portion 3.

Furthermore, the number of magnets disposed in the moving portion is not limited to the number described in the first embodiment.

Furthermore, the lightening portion provided in the fixing portion does not need to pass through the outer circumferential side in the radial direction as long as a magnet may be installed.

Furthermore, instead of the lens held by the rear frame portion 5, an image sensor may also be used. In this case, in the direction along the optical axis, the distance from the position on the extreme object side of the moving-side sliding surface 31c in the moving portion 3 to the position of the extreme image side is longer than the distance from the emission surface of the object-side fixed lens group Gf held by the front frame portion 4 to the light-receiving surface of the image sensor.

According to the present disclosure, it is possible to secure a stable operation while maintaining a reduction in size and weight of the actuator that moves the moving lens forward and backward.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical unit comprising:
    a fixing portion including:
        a front frame configured to hold an object-side fixed lens group,
        a rear frame configured to hold that holds one of an image-side fixed lens group or an image sensor, and
        a fixing portion main body formed from a non-magnetic material and configured to hold the front frame and the rear frame;
    a moving frame configured to hold a moving lens group between the object-side fixed lens group and one of the image-side fixed lens group or the image sensor, the moving frame being arranged on an inner side of the fixing portion main body in a radial direction so as to be slidable with respect to the fixing portion main body; and
    a voice coil motor configured to move the moving frame along a direction of the optical axis relative to the fixing portion main body, the voice coil motor including:
        a magnetic portion arranged in the moving frame, the magnetic portion being magnetized in a direction intersecting an optical axis of the object-side fixed lens group, and
        a coil arranged in the fixing portion main body, the coil being located on an outer side of the fixing portion main body in the radial direction with respect to the magnetic portion;
    wherein a total weight of the moving frame including the moving lens group and the magnetic portion is in a range of 20 mg and 100 mg; and
    a driving force of the voice coil motor is in a range of 40 mgf and 1000 mgf.

2. The optical unit according to claim 1, wherein a minimum distance between the fixing portion main body and the magnetic portion is equal to or less than 0.5 mm.

3. The optical unit according to claim 1, wherein one of the front frame and the rear frame having a smaller minimum distance from the magnetic portion is formed by using a non-magnetic material.

4. The optical unit according to claim 2, wherein the front frame and the rear frame have the minimum distance equal to or less than 0.5 mm from the magnetic portion and are formed by using a non-magnetic material.

5. The optical unit according to claim 1, wherein the non-magnetic material is austenitic stainless steel.

6. The optical unit according to claim 1, wherein the non-magnetic material has been subjected to surface treatment using electroless nickel with a content rate of phosphorus equal to or greater than 5%.

7. The optical unit according to claim 1, wherein the non-magnetic material is aluminum.

8. The optical unit according to claim 1, wherein the non-magnetic material is a resin material.

9. The optical unit according to claim 1, wherein the non-magnetic material is titanium.

10. The optical unit according to claim 1, wherein the moving frame is formed by using a non-magnetic material.

11. The optical unit according to claim 10, wherein the moving frame is formed by using aluminum.

12. The optical unit according to claim 1, further comprising a biasing member having a ferromagnetic material that biases the moving portion in a direction toward the fixing portion main body by applying an attraction force due to magnetism between the biasing member and the magnetic portion.

13. The optical unit according to claim 1, wherein, in the direction along the optical axis, the distance from a position on an extreme object side of a moving-side sliding surface of the moving frame to a position on an extreme image side is longer than a distance from an emission surface of the object-side fixed lens group held by the fixing portion to one of an incident surface of the image-side fixed lens group or to a light-receiving surface of the image sensor.

14. The optical unit according to claim 1, wherein, when viewed from the front frame in the direction of the optical axis, one or more of a part of the moving frame, a part of the coil, or a part of the magnetic portion is included inside the front frame portion.

15. An endoscope that is inserted into a subject and that observes an interior of the subject, the endoscope comprising the optical unit according to claim 1.

* * * * *